US012710355B2

(12) United States Patent
Bozhevolnyi et al.

(10) Patent No.: US 12,710,355 B2
(45) Date of Patent: Aug. 18, 2026

(54) SYSTEM FOR TISSUE ANALYSIS

(71) Applicants: SINTEF TTO AS, Trondheim (NO); Syddansk Universitet, Odense (DK)

(72) Inventors: Sergey I. Bozhevolnyi, Odense (DK); Chao Meng, Odense (DK); Fei Ding, Odense (DK); Paul Conrad Vaagen Thrane, Oslo (NO); Aliaksandr Bykau, Oulu (FI); Igor Meglinski, Oulu (FI)

(73) Assignees: SINTEF TTO AS, Trondheim (NO); Syddansk Universitet, Odense (DK)

( * ) Notice: Subject to any disclaimer, the term of this patent is extended or adjusted under 35 U.S.C. 154(b) by 153 days.

(21) Appl. No.: 18/639,086

(22) Filed: Apr. 18, 2024

(65) Prior Publication Data

US 2024/0353319 A1 Oct. 24, 2024

(51) Int. Cl.
*G01N 21/21* (2006.01)
*G01N 33/483* (2006.01)

(52) U.S. Cl.
CPC ......... *G01N 21/21* (2013.01); *G01N 33/4833* (2013.01)

(58) Field of Classification Search
CPC ........................... G01N 21/21; G01N 33/4833
See application file for complete search history.

(56) References Cited

U.S. PATENT DOCUMENTS 10,545,348 B1 1/2020 Lu et al.
2009/0237785 A1 9/2009 Bloom
2013/0307950 A1* 11/2013 Aharon .............. G01N 21/4738 348/65
2014/0085693 A1 3/2014 Mosallaei et al.
2020/0341180 A1 10/2020 Chen-Ho et al.
2021/0307607 A1 10/2021 Yamane
2022/0035002 A1 2/2022 Davis et al.
2022/0099861 A1 3/2022 Li et al.
2023/0072722 A1* 3/2023 Bozhevolnyi .......... G02B 5/008
2024/0295497 A1* 9/2024 Lucente ............. G01N 21/7743

FOREIGN PATENT DOCUMENTS

WO WO-2023041916 A1 3/2023

OTHER PUBLICATIONS

Bakke et al., "A robust, non-resonant piezoelectric micromirror", SINTEF ICT, 171-172 (2021).
Bakke et al., "PZT micromirror with integrated piezoresistive position sensors", Sintef Ict, 192-193 (2021).

(Continued)

*Primary Examiner* — Hina F Ayub
(74) *Attorney, Agent, or Firm* — MARSHALL, GERSTEIN & BORUN LLP

(57) ABSTRACT

A system for analyzing a cell or tissue sample using polarized light, the system comprising: an apparatus for adjustably changing the polarization state of incident light having at least a first wavelength containing a first polarization state and a second polarization state; a light source arranged to provide the incident light to the apparatus; and a polarimeter, wherein the apparatus is arranged to direct polarized light onto a cell or tissue sample, and the polarimeter is arranged to receive light reflected from the cell or tissue sample, and measure the polarization state of said light.

17 Claims, 19 Drawing Sheets

(56) References Cited

OTHER PUBLICATIONS

Borokovka et al., Screening of Alzheimer's disease with multiwavelength stokes polarimetry in a mouse model, IEEE Transactions on Medical Imaging, 41(4):977-82 (Apr. 2022).
Ding et al., "Gradient metasurfaces: a review of fundamentals and applications", Reports on Progress in Physics, 81(2): 26401 (2017).
Ding et al., Metasurface-based polarimeters, Appl. Sci., 8:594 (2018).
Dremin et al., Histological imaging of unstained cancer tissue samples by circularly polarized light, Proceedings of the SPIE, vol. 11919, id. 119190F (Dec. 2021).
International Seach Report and Written Opinion, International Application No. PCT/GB2022/052337, mailed Dec. 23, 2022.
Ivanov et al., Colon cancer detection by using Poincare sphere and 2D polarimetric mapping of ex vivo colon samples, J. Biophotonics, 13:e202000082 (2020).
Ivanov et al., Polarization and depolarization metrics as optical markers in support to histopathology of ex vivo colon tissue, Biomedical Optics Express, 12(7):4560-72 (Jul. 2021).
Ivanov et al., Polarization-based histopathology classification of ex vivo colon samples supported by machine learning, Frontiers in Physics, vol. 9, Article 814787 (Jan. 2022).
Meng et al., "Full-range birefringence control with piezoelectric MEMS-based metasurfaces", Nature Communications, 1-21 (2021).
Meng et al., "Dynamic piezoelectric MEMS-based optical metasurfaces", Science Advances, 1-12 (2021).
Plum, "Extrinsic chirality: Tunable optically active reflectors and perfect absorbers", Applied Physics Letters, American Institute of Physics, 108(21): 241905 (2016).
Thrane et al., "Dynamic metasurfaces for 3D imaging (3D-META)", SINTEF Microsystems and Nanotechnology, 1-5 (2020).

* cited by examiner

800

SYSTEM FOR TISSUE ANALYSIS

FIELD OF THE DISCLOSURE

The present invention relates to a system and method for analyzing biological samples using polarized light. In particular the system and method employ an adjustable waveplate for conveniently changing the polarization state of incident light.

BACKGROUND

Accurate diagnosis of cancer in tissue relies on labor intensive sample preparation after which specialists are required to give a diagnosis through microscopy imaging. Despite the effort involved, the rates of conclusive diagnosis by histological analysis for a range of the most dangerous cancers is only 65-75%.

Novel techniques and approaches are being constantly sought to assist medical doctors and to increase both sensitivity and specificity of the existing diagnostic methods. In such context, ex vivo tissue polarimetry holds promise to become a valuable optical diagnostic technique as it is sensitive to tissue alterations caused by different benign and malignant formations.

The way polarized light is backscattered from a tissue is highly sensitive to structural alternations within the cell or tissue which may be caused by a pathology or be indicative of a certain developmental state or indicative of some other property. For example, cancers tend to cause an increase in size of the nucleus and Alzheimer's disease (AD) causes a growth of Aβ plaques and neurofibrillary tangles. Such structural changes will change the scattering pattern of polarized light applied thereto and therefore images of light reflected from a tissue or other biological sample will differ between healthy and diseased samples. Such differences can be exploited in diagnosis, staging, prognosis, monitoring etc. of a disease in a patient.

For example, it has been shown (Ivanov, D. et al., in Frontiers in Physics, Jan. 24, 2022, doi: 10.3389/fhpy. 2021. 814787) how polarized light can be used to distinguish between healthy and tumor samples in a study of ex vivo colon samples.

Beyond cancer, it has also been shown (Borovkova, M. et al., IEEE Transactions on Medical Imaging, vol. 41, No. 4, April 2022) how polarimetry allows characterization of unstained brain tissue at different stages of AD; as Aβ plaques increased with disease progression so the sample exhibited higher birefringence due to the fibrous nature of the Aβ plaques.

The above techniques show the potential of polarized light in clinical contexts. However, the polarized light applied to the samples in these cases was generated using half wave and quarter wave plates. At present, waveplates are fabricated to achieve a specific output, for example, a waveplate may be configured as a half wave plate, or a quarter wave plate. In applications in which the desired polarization state of the output may change, it is typically necessary to swap between different waveplates, or rotate one or more components with respect to each other. This not only limits the speed of operation, but also requires a suitable mechanical arrangement to deploy multiple different waveplates, and/or motors to rotate optical components, the cost of which can be significant. Such mechanical arrangements are also typically relatively large, heavy and may not be fully reliable.

In clinical diagnosis and related studies, it is desirable to be able to vary the state of the polarized light which is applied to the sample and/or to readily obtain images and data from a sample using polarized light in different states. In other words, it is desirable to have rapid control of the polarization state of the light which illuminates a sample allowing more information to be gathered in a given time period. The more information that is gathered, the better the chance of identifying polarization states that show a significant difference between healthy and unhealthy tissue. Such objectives are not conveniently achievable with the prior art systems.

SUMMARY

According to a first aspect of the invention there is provided a system for analyzing a cell or tissue sample using polarized light, the system comprising:

- an apparatus for adjustably changing the polarization state of incident light having at least a first wavelength containing a first polarization state and a second polarization state;
- a light source arranged to provide the incident light to the apparatus; and
- a polarimeter,
- wherein the apparatus is arranged to direct polarized light onto a cell or tissue sample, and the polarimeter is arranged to receive light reflected from the cell or tissue sample, and measure the polarization state of said light,
- wherein the apparatus comprises:
  - a polarization changing optical metasurface (OMS) arranged to reflect and/or transmit light of a first polarization state according to a first reflection/transmission factor, and to reflect and/or transmit light of a second polarization state according to a second reflection/transmission factor, said second polarization state being different to said first polarization state, and said second reflection/transmission factor being different to said first reflection/transmission factor; and
  - a mirror arranged to reflect the transmitted light of the second polarization state, wherein the apparatus is arranged to move the mirror and/or the polarization changing OMS relative to one another to alter a separation between the polarization changing OMS and the mirror, thereby altering a phase difference between the light reflected by the polarization changing OMS and the light reflected by the mirror such that a combined polarization state of light reflected by the apparatus is adjustable.

The apparatus is arranged to direct the reflected light, having a combined polarization state as described herein, onto the cell or tissue sample.

According to a second aspect of the invention, there is provided a method of analyzing a cell or tissue sample using polarized light, the method comprising: providing incident light from a light source having at least a first wavelength containing a first polarization state and a second polarization state;

- reflecting and/or transmitting light from said incident light having a first polarization state, according to a first reflection/transmission factor, with a polarization changing optical metasurface (OMS);
- reflecting and/or transmitting light from said incident light having a second polarization state, according to a second reflection/transmission factor, with said polarization changing OMS, said second polarization state being different to said first polarization state and said second reflection/transmission factor being different to said first reflection/transmission factor;

reflecting the transmitted light of the first and/or second polarization states with a mirror;

moving the mirror and/or the polarization changing OMS in order to alter a separation between the polarization changing OMS and the mirror thereby altering a phase difference between the light reflected by the polarization changing OMS and the light reflected by the mirror such that a combined polarization state of light reflected by both the polarization changing OMS and the mirror is adjusted;

directing the light reflected by the OMS and the mirror which has a combined polarization state onto said cell or tissue sample;

reflecting light from the cell or tissue sample onto a polarimeter; and measuring the polarization state of said reflected light to analyze the cell or tissue sample.

According to a third aspect of the invention is provided a use of a system of the invention as defined herein for analyzing a cell or tissue sample.

It will be understood that the reflection/transmission factors are used as a means of concisely explaining the reflection/transmission properties of the OMS. As such, the reflection/transmission factors may be defined in any suitable way. For example, the reflection/transmission factor may be defined as the percentage of light of a certain polarization state which the OMS is configured to transmit, e.g., an OMS with a first reflection/transmission factor of 60% may be configured to transmit 60% of light of the first polarization state and configured to reflect 40% of light of the first polarization state. Alternatively, the reflection/transmission factor may be defined as the percentage of light of a certain polarization state which the OMS is configured to reflect. It will further be understood that the 60%, 40% example given above is simplified for the purposes of explanation, and that in reality, there will be a degree of scattering and/or absorption such that the percentage of light reflected, and the percentage of light transmitted do not add up to 100%.

It will be understood that the light which is received by the polarimeter may be reflected from the cell or tissue sample directly from the point of illumination on the cell or tissue sample (the point at which the incident light strikes the sample). Alternatively, the light which is received by the polarimeter may be reflected from a point (or points) on the sample which is spaced from the point of illumination such that the light has propagated a distance through the sample before being reflected.

In embodiments, when analyzing a cell sample, light is collected which has been reflected from the point of illumination, and when analyzing a tissue sample, light is collected which has been reflected from a point (or points) on the sample which is spaced from the point of illumination.

Thus, it will be seen by those skilled in the art that in accordance with the invention, an adjustable polarization changing structure can be used to provide different polarizations for analyzing a cell or tissue sample without needing to provide a complex optical set-up comprising a plurality of different wave plates which need to be reconfigured when a different polarization state is needed. Moreover, since the overall polarization state may be dependent only on the separation of the mirror and the OMS, a greater number of different states may be achievable. For example, by adjusting the separation between the polarization changing OMS and the mirror in a continuous fashion, the polarization state of the overall reflected light can be continuously adjusted. As such, it is possible to create a system which is both portable enough to be used outside of a laboratory, for example, in a clinical setting such as a doctor's or nurse's office, and also able to be operated without needing to understand how to set up complex optical elements. In one example, it has been shown that circular polarization may give an advantage in contrast, and being able to switch between two circular incident states may improve the signal to noise ratio. For this advantage to be realized in a practical setting, the polarization state switching needs to happen quickly, which is achievable using the system and method of the invention.

The polarization state of the light reflected by the sample may be assessed (via the polarimeter) using Artificial Intelligence (AI) and machine learning to process extensive data on the polarization state of the reflected light and therefore the properties of the sample. For example, in embodiments support vector machine learning may be used for fast implementation of supervised learning for pattern recognition. This may provide an estimation of parameters such as distributions and packaging density of cells, nuclear and structural malformations based on the signature of polarized light which is reflected from the sample.

In this way, there may be no need for expert analysis of the results as a computer can compare results to reference samples, e.g., healthy and diseased samples. This enables the system of the invention to be deployed widely in clinical settings. The system of the invention may be particularly useful in screening applications, where high-level analysis can be performed automatically, and borderline cases can then be referred to an expert for detailed analysis.

In embodiments, the apparatus is a waveplate apparatus.

The light source of the system may emit polarized or unpolarized light. In a set of embodiments, the light source is configured to emit linearly polarized light. In a further set of embodiments, the light source is configured to emit circularly polarized light. In a further set of embodiments, the light source is configured to emit elliptically polarized light.

In embodiments, the system comprises a sample stage configured to support the cell or tissue sample. In embodiments, the sample stage is a sample translation stage and is configured to translate (i.e., move) the sample such that the light can be made incident on different points on the sample. This may allow the build-up of a polarimetric image map, by point-by-point polarimetric measurement. In embodiments, the system may be arranged to scan the light across the sample (e.g., using the movement of the mirror, or by moving (tilting) the apparatus using an apparatus moving mechanism). In such embodiments, the sample stage may be a stationary plinth.

In a set of embodiments the OMS is configured so that it predominantly reflects light of the first polarization, transmits light of the second polarization, independent of the separation between the OMS and the mirror.

In a set of embodiments, the apparatus is arranged such that said separation between the OMS and the mirror has a minimum value of at least 50 nm. In a further set of embodiments, the separation between the OMS and the mirror is at least 75 nm. In a set of embodiments, the apparatus is arranged such that the separation between the OMS and the mirror has a minimum value of at least 10% of the incident wavelength, i.e., the first wavelength. Where the incident light comprises a plurality of wavelengths, the first wavelength may be the shortest wavelength of the incident light.

In a set of embodiments, the apparatus is arranged such that the separation between the polarization changing OMS and the mirror has a maximum value of at most ten wavelengths, e.g., at most five wavelengths, e.g., one wavelength.

In a set of embodiments, the apparatus is arranged to alter the separation between the polarization changing OMS and the mirror between respective minimum and maximum values which differ by a value dependent on the largest wavelength of the incident light. In embodiments, the apparatus is arranged to alter the separation between the polarization changing OMS and the mirror between respective minimum and maximum values which differ by at least 700 nm, e.g., 725 nm; or by at least 450 nm, e.g., 425 nm. In one set of examples the minimum separation is 75 nm. In a set of examples the maximum separation is less than 1000 nm, e.g., 800 nm or less than 600 nm, e.g., 550 nm.

In a set of embodiments the apparatus is arranged to be able to alter the separation between the polarization changing OMS and the mirror between respective minimum and maximum values which differ by at least 9/10 of the first wavelength, or by at least 6/10 of the first wavelength. In one set of examples the minimum separation is 1/10 of the first wavelength.

In a set of embodiments, the OMS is arranged to predominantly reflect light of the first polarization state, and to predominantly transmit light of the second polarization state, but more particularly, in a set of embodiments, the OMS is arranged to transmit less than 10%, e.g., less than 5% of the light of the first polarization state. In an overlapping set of embodiments, the OMS is arranged to transmit more than 40% e.g., more than 50%, more than 60% or more than 70% of the light of the second polarization state. It will be understood that a proportion of the incident light may be absorbed by the OMS and by the mirror.

The OMS may be configured to achieve the respective reflection and transmission of the first and second polarization states with many different polarization states, having many different relationships between the polarization states, but in a set of embodiments, the OMS is arranged such that the first polarization state is orthogonal to the second polarization state.

In a set of embodiments said first wavelength of the incident light is 400 to 900 nm, e.g., 500 to 800 nm, e.g., 600 to 700 nm. In a preferred set of embodiments, the first wavelength is about or is 640 nm.

The OMS may be constructed of any suitable material such as any suitable metal, for example, the OMS may be constructed from aluminum. However, in a set of embodiments, the OMS is constructed from gold.

The OMS may be constructed of a plurality of individual nanostructures. In a set of embodiments the nanostructures form a periodically repeating pattern. In a set of such embodiments the spatial period of the repeating pattern is less than the first wavelength.

In a set of embodiments the nanostructures have dimensions which are all less than the first wavelength.

In a set of embodiments, the nanostructures are each cuboidal in shape, and have a thickness which is smaller than both their length and width. It will be understood that the thickness of the nanostructures is measured along the axis which is substantially parallel to the direction of the incident light which the OMS is configured to manipulate. It will similarly be understood that the length and width of the nanostructures are measured in the plane which is substantially perpendicular to the direction of the incident light which the OMS is configured to manipulate.

The apparatus may adjust the separation between the OMS and the mirror by moving the OMS whilst keeping the mirror stationary, but in a set of embodiments, the apparatus is arranged to move the mirror relative to the OMS. In such a set of embodiments, the apparatus may further be arranged to move the OMS relative to the mirror, or to keep the OMS stationary relative to the mirror.

In embodiments where the apparatus is configured to move the mirror relative to the OMS, the mirror may be moved by any suitable means. However, in a set of embodiments, the mirror is a Micro-electromechanical systems (MEMS) mirror which is translatable upon application of a suitable voltage. In a set of embodiments the mirror comprises a feedback mechanism, e.g., a capacitive, optical, or piezoresistive feedback mechanism to regulate its separation from the OMS and/or its degree of planarity.

The mirror may be constructed from any suitable material, however, in a set of embodiments, the mirror is constructed from gold.

The polarimeter may be a metasurface-based polarimeter. For example, as described by Ding et al., in Applied Sciences (2018), 8 (4), 594.

The polarimeter may be arranged to receive light directly from the cell or tissue sample, however, in embodiments, the system may comprise collection optics (e.g., one or more lenses, e.g., one or more objective lenses) arranged to collect light reflected from the cell or tissue sample and direct said light onto the polarimeter.

In a set of embodiments, the system may comprise a plurality of apparatuses as described herein. In such embodiments, the apparatuses may be arranged such that incident light is reflected from a first apparatus, and then subsequently reflected from a second apparatus (i.e., in a serial arrangement). Alternatively or additionally, light from the light source could be divided into a plurality of beams, for example, by any known beam splitter, with each beam being reflected by a spate apparatus, before interferometrically recombining (i.e., in a parallel arrangement). Such embodiments may enable more complex polarization changes and beam properties to be realized.

In a set of embodiments, the system is arranged to alter an angle of incidence of the polarized light onto the cell or tissue sample. In embodiments, the system comprises a tilt-able mount on which the apparatus is mounted, said mount being configured to alter the angle of the apparatus relative to the cell or tissue sample and hence alter the angle of incidence of the polarized light on the sample. In other embodiments the angle of incidence may be controlled by altering the angle of the mirror of the apparatus. Altering the angle of incidence may affect the penetration depth which the polarized light is able to reach within the sample. In embodiments where the system is arranged to alter the angle of incidence, the system may also be arranged to alter the position of the polarimeter and/or collection optics (where provided).

In a set of embodiments, the system may comprise additional optical elements (e.g., collection optics). For example, the system may additionally comprise an OMS element through which the light is transmitted. Such an OMS element may be configured to further alter the properties of the light. In embodiments, the system may comprise one or more filters.

In the current disclosure, it will be understood that a polarization changing optical metasurface (OMS) is an artificial sheet material having sub-wavelength thickness, and sub-wavelength scaled patterns in the planar dimensions which are formed by nanostructures. The polarization changing OMS has differing transmission and reflection properties for different polarization states and is able to manipulate radiation wavefronts at a subwavelength scale.

The cell or tissue sample may be any human or other animal sample of interest, including cell samples where the cell membranes are only partially or not at all intact, such that the cell contents and/or extracellular matrix or other extracellular components are assessed.

In embodiments the sample has not been stained and no contrast agents have been applied. This can simplify the sample preparation step as compared to traditional methods of histopathology. In embodiments the samples have a depth of 0.5 to 10 mm, e.g., 2 to 7 mm. In other embodiments, the samples may be thin histological slices which may have a thickness of 2 to 10 μm.

Where the sample is to be used to make a diagnosis, prognosis or otherwise investigate the health of a subject, the sample will typically have been taken as a biopsy or as a result of another surgical procedure. The system of the present invention may be used to analyze samples from patients having or suspected of having a tumor. The sample may be from any organ or region of the body, e.g., the colon, stomach, breast, pancreas, prostate, kidney, lung etc.

Any type of sample which in a disease state has physical characteristics which are different from a healthy state, and those physical differences impact on the properties of polarized light reflected therefrom, can be analyzed according to the present invention. For example, the increase in nuclear size in cancerous cells will result in a change of scattering pattern and an increase of the scattering anisotropy that can be interpreted as the increase of Mie over the Rayleigh contribution to the total tissue scattering. The changes of anisotropy of scattering can be observed by tracking the Stokes vector in relation to the Poincaré sphere. This kind of change can be detected and quantified using the system and method of the present invention. In particular, scattering changes can be seen via the degree of polarization or Stokes parameters. A specific combination of these parameters may serve as markers of diseases.

The ability of polarized light studies to distinguish between healthy and tumor tissue has been demonstrated by Ivanov et al., in Frontiers in Physics, Jan. 24, 2022, doi: 10.3389/fphy. 2021. 814787, by Ivanov et al., in J. Biophotonics (2020); 13.8: e.202000082, and by Ivanov et al., in "Polarization and depolarization metrics as optical markers in support to histopathology of ex vivo colon tissue," Biomed. Opt. Express 12, 4560-4572 (2021) the disclosures of which are incorporated herein by reference. These papers describe the type of polarimetric quantities which may be assessed according to the present invention and used as predictors of disease. According to the present invention, and as described in these papers, analysis of the samples (e.g., differentiation of healthy versus diseased tissue) can be done using Poincaré sphere and 2D polarimetric mapping.

The ability of the system and method of the invention to discern structural irregularities and changes in a cell or tissue sample has utility in many clinical scenarios other than cancer. For example, in Alzheimer's Disease where the presence of Aβ plaques and neurofibrillary tangles in the brain tissues increases the inhomogeneity of the refractive index, increases the scattering coefficient, increases the birefringence due to parallel alignment of fibrils in the amyloid plaques and increases the anisotropy of scattering that is detected via the polarization measurements. The sample may therefore be brain tissue.

The measurable changes in polarization (e.g., changes in polarization state or degree of polarization, e.g., depolarization) of reflected light caused by malformations in diseased cells or tissue can be used as diagnostic markers.

The samples are typically ex vivo samples, however the system of the invention could be used for in vivo measurements, such as in the analysis of moles.

Thus, according to a fourth aspect of the invention, there is provided a system for analyzing a body area using polarized light, the system comprising:

an apparatus for adjustably changing the polarization state of incident light having at least a first wavelength containing a first polarization state and a second polarization state;

a light source arranged to provide the incident light to the apparatus; and a polarimeter, wherein the apparatus is arranged to direct polarized light onto a body area, and the polarimeter is arranged to receive light reflected from the body area, and measure the polarization state of said light, wherein the apparatus comprises:

a polarization changing optical metasurface (OMS) arranged to reflect and/or transmit light of a first polarization state according to a first reflection/transmission factor, and to reflect and/or transmit light of a second polarization state according to a second reflection/transmission factor, said second polarization state being different to said first polarization state, and said second reflection/transmission factor being different to said first reflection/transmission factor; and a mirror arranged to reflect the transmitted light of the second polarization state, wherein the apparatus is arranged to move the mirror and/or the polarization changing OMS relative to one another to alter a separation between the polarization changing OMS and the mirror, thereby altering a phase difference between the light reflected by the polarization changing OMS and the light reflected by the mirror such that a combined polarization state of light reflected by the apparatus is adjustable.

According to a fifth aspect of the invention, there is provided a method of analyzing a body area using polarized light, the method comprising: providing incident light from a light source having at least a first wavelength containing a first polarization state and a second polarization state;

reflecting and/or transmitting light from said incident light having a first polarization state, according to a first reflection/transmission factor, with a polarization changing optical metasurface (OMS);

reflecting and/or transmitting light from said incident light having a second polarization state, according to a second reflection/transmission factor, with said polarization changing OMS, said second polarization state being different to said first polarization state and said second reflection/transmission factor being different to said first reflection/transmission factor;

reflecting the transmitted light of the first and/or second polarization states with a mirror;

moving the mirror and/or the polarization changing OMS in order to alter a separation between the polarization changing OMS and the mirror thereby altering a phase difference between the light reflected by the polarization changing OMS and the light reflected by the mirror such that a combined polarization state of light reflected by both the polarization changing OMS and the mirror is adjusted;

directing the light reflected by the OMS and the mirror which has a combined polarization state onto said body area;

reflecting light from the body area onto a polarimeter; and measuring the polarization state of said reflected light to analyze the body area.

According to a sixth aspect of the invention is provided a use of a system of the invention as defined herein for analyzing a body area.

Embodiments of other aspects of the invention described herein apply, mutatis mutandis, to these aspects of the invention which involve in vivo analysis of a body area of a human or other animal. In embodiments the body area is the skin, including moles and skin tags. In other embodiments the body area is the eye. Such analysis may be useful in screening and diagnosis, e.g., for cancer.

The features described above in relation to different aspects and embodiments of the present invention may be combined in various combinations. It will be understood that the combination of features in the following description and drawings are intended to be illustrative, and are non-limiting.

BRIEF DESCRIPTION OF THE DRAWINGS

An embodiment of the invention will now be described, by way of example only, with reference to the accompanying drawings in which.

DETAILED DESCRIPTION

In the below description, terms such as raised, high, low, height, and top are used. It will be understood that these terms refer to the orientation of the accompanying drawings, in which the light incident on the waveplate apparatus originates from the top of the drawings in FIGS. 1 and 5.

Figure 1:
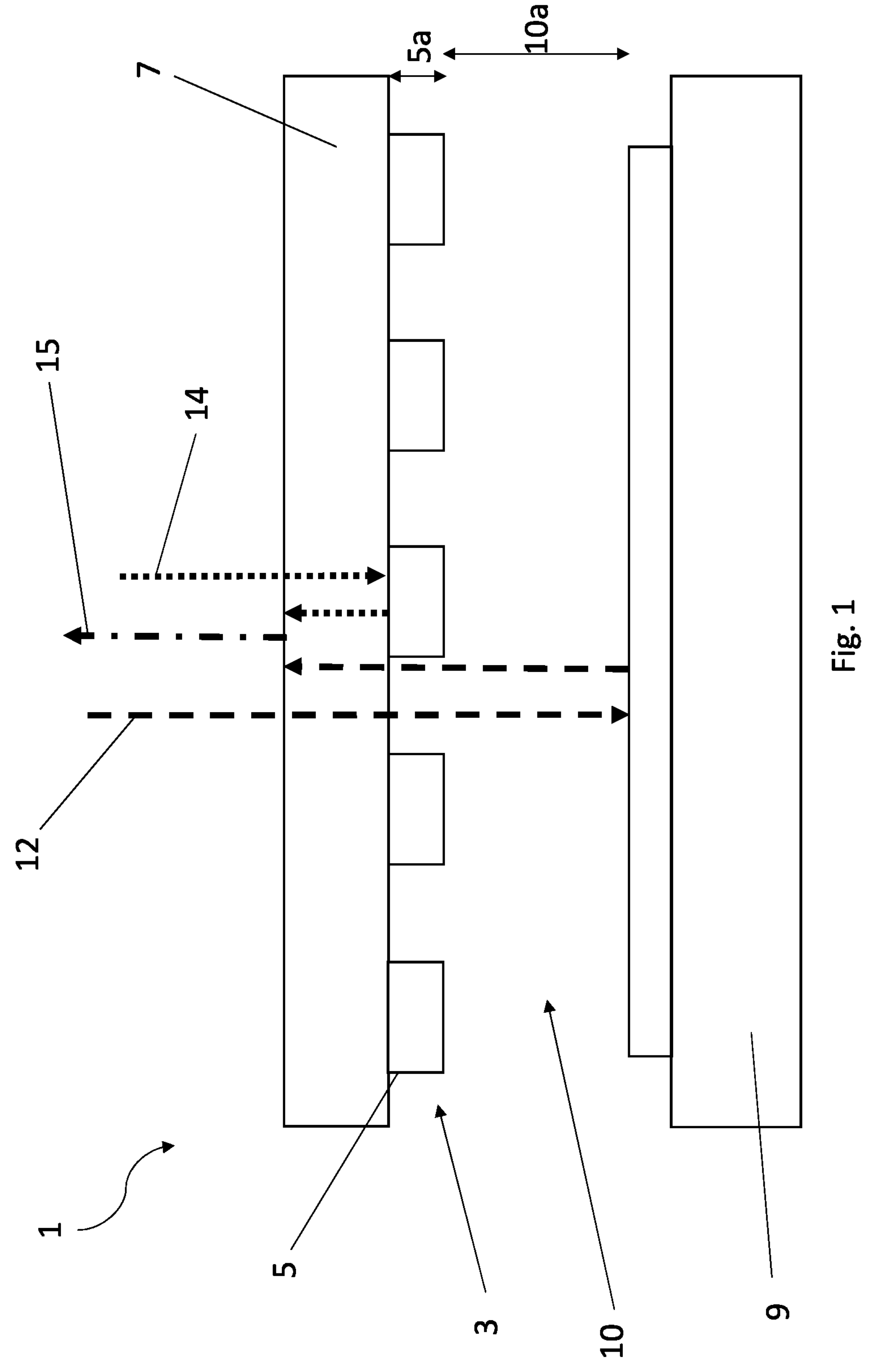
FIG. 1 is a schematic diagram of an apparatus which forms a part of the system of the present invention.

FIG. 1 is a schematic diagram of a waveplate apparatus 1 according to an embodiment of the invention. The waveplate apparatus 1 comprises an optical metasurface (OMS) 3 which is comprised of a plurality of nanostructures 5. The structure of the OMS 3 is discussed in detail below. The OMS 3 is mounted on a glass substrate 7 such that the incident light passes through the glass substrate before reaching the OMS 3. The substrate 7 provides mechanical protection of the device from the environment. Use of glass is not essential—other optically transmissive materials could be used depending on the wavelengths of light being used. For example, in other embodiments a silicon substrate could be used as this is typically transmissive in the infra-red range. This could be advantageous in allowing the OMS to be mounted on a MEMS actuator with the mirror remaining static.

Anti-reflective coatings can be used on the surface of the substrate 7 in order to increase the efficiency of device by reducing unwanted reflection, for example, from the surface of the substrate 7 which incident light first encounters before reaching the OMS 3.

The waveplate apparatus 1 further comprises a mirror 9 which in the illustrated embodiment is an ultra-flat MEMS mirror having a gold reflective surface The mirror is, for example, constructed as described in Bakke, Thor, and Ib-Rune Johansen. "A robust, non-resonant piezoelectric micromirror." 16$^{th}$ *International Conference on Optical MEMS and Nanophotonics*. IEEE, 2011, the contents of which is incorporated herein by reference. The mirror 9 is designed to move across the range from a minimum separation of 75 nm from the OMS 3 to a maximum separation of 600 nm from the OMS 3. Further, if the resting position of the mirror, when there is no voltage actuating the mirror, is more than 600 nm away from the OMS 3, then the mirror 9 must also be designed to move across the distance between the resting position and 600 nm, in addition to moving across the separation range from 600 nm to 75 nm. The abovementioned range of movement can be achieved with a driving voltage of up to two volts.

To get the same polarization change across the whole device it is advantageous to have the reflecting surface of the mirror as flat as possible, to within 20 nm across the whole area which overlaps the OMS 3. There may be small (compared to the OMS area) particles or uneven areas that exceed this height difference, but they should not protrude so far above the surface that they physically hinder the movement of the mirror.

The space between the OMS 3 and the mirror 9 forms a gap 10. The MEMS mirror 9 is configured to move relative to the substrate 7 and OMS 3 upon application of a suitable voltage such that the size 10*a* of the gap 10 between the OMS and the mirror 9 can be adjusted. In FIG. 1, light incident on the waveplate apparatus 1 is shown to contain light which is linearly polarized along the Y axis 12, and light which is linearly polarized along the X axis 14. The figure also shows the light 15 which Is reflected by the waveplate apparatus 1. It will be understood that the reference numerals 12 and 14 refer to the light which is linearly polarized along the Y and X axis respectively. The reference numerals do not refer to the X and Y axes themselves. The X and Y axes referred to herein are orthogonal and lie in the plane of the OMS 3 as shown in FIG. 2.

Figure 2:
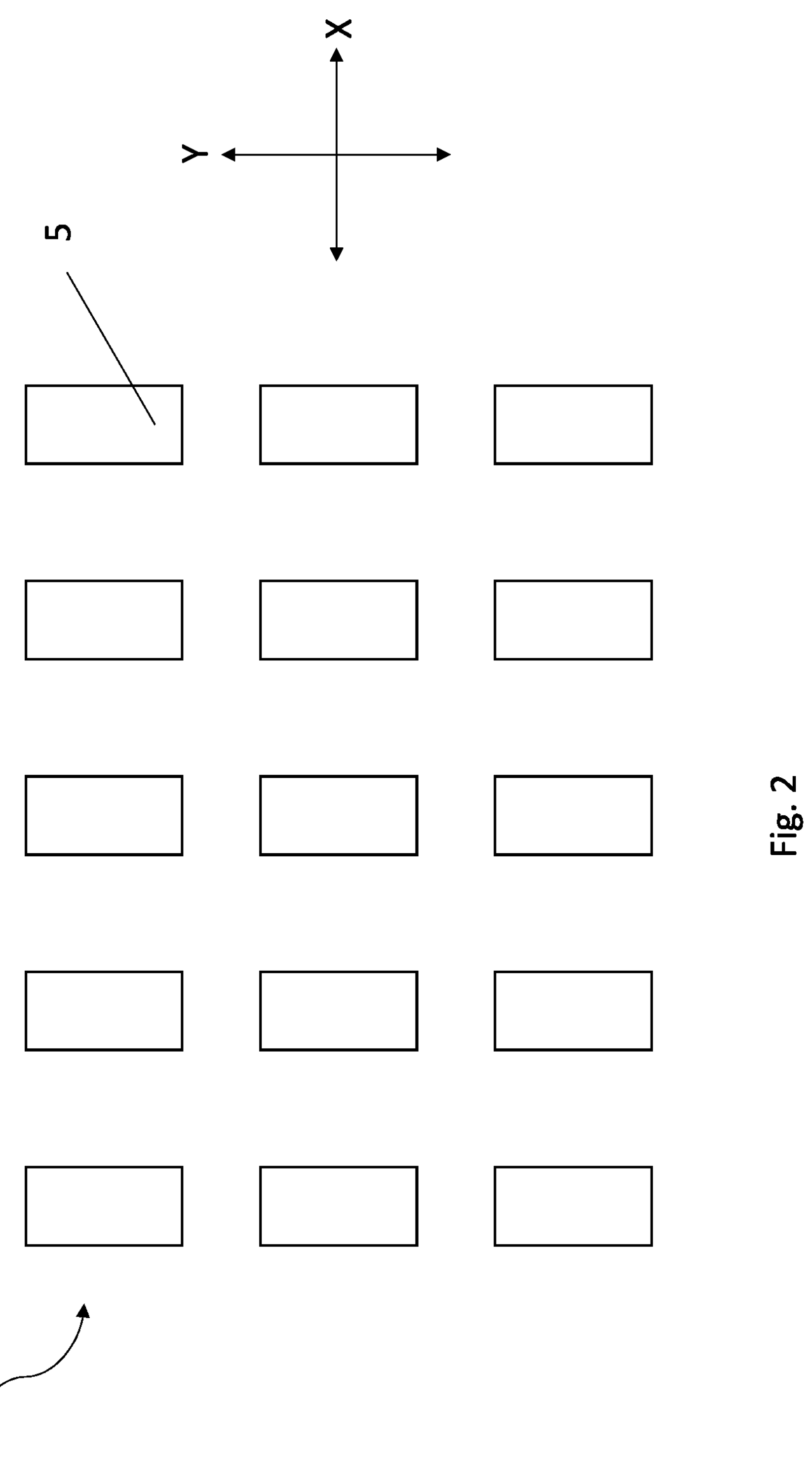
FIG. 2 is a schematic top-down view of an optical metasurface.

FIG. 2 is a highly schematic diagram of the OMS 3 showing the individual nanostructures 5. These nanostructures have both length and width less than the wavelength of the incident light. There are arranged in a periodically repeating pattern in two directions (horizontally and vertically). Each of the spatial periods is also less than the wavelength of the incident light.

The OMS can be configured to reflect and/or transmit light of a first polarization state according to a first reflection/transmission factor, and to reflect and/or transmit light of a second polarization state according to a second reflection/transmission factor, said second polarization state being different to said first polarization state, and said second reflection/transmission factor being different to said first reflection/transmission factor. In the illustrated embodiment of FIG. 2, the OMS 3 is configured to predominantly transmit light which is polarized linearly along the Y axis, and reflect light which is polarized linearly along the X axis. As such, when light linearly polarized along the X and Y axes is incident on the OMS 3, the OMS 3 transmits light which is polarized linearly along the Y axis 12, and reflects light which is polarized linearly along the X axis 14. The inventors have appreciated that whilst transmission and reflection will not in practice be perfect, priority when designing the OMS 3 should be to achieve low transmission (for example, less than 5%) of one polarization state (light linearly polarized in the X axis 14 in the illustrated embodiment), with high transmission of the other polarization state (light linearly polarized along the Y axis 12 in the illustrated embodiment) being a secondary consideration. This is illustrated with reference to FIG. 3.

In the embodiment of FIG. 2, each nanostructure is made of gold, and has dimensions of 200 nm by 80 nm, with a thickness of 50 nm. The nanostructures 5 are arranged in a 2-dimensional array with a periodicity of 250 nm. The specific configuration in the illustrated embodiment is designed to perform best when the incident light is monochromatic and has a wavelength of 800 nm. It will be understood that although the specific embodiment being described is designed to perform best when the incident light has a wavelength of 800 nm, the invention is applicable using incident light of a wide range of wavelengths. In particular, the use of incident light having greater wavelengths may help to realize deeper tissue penetration.

Figure 3:
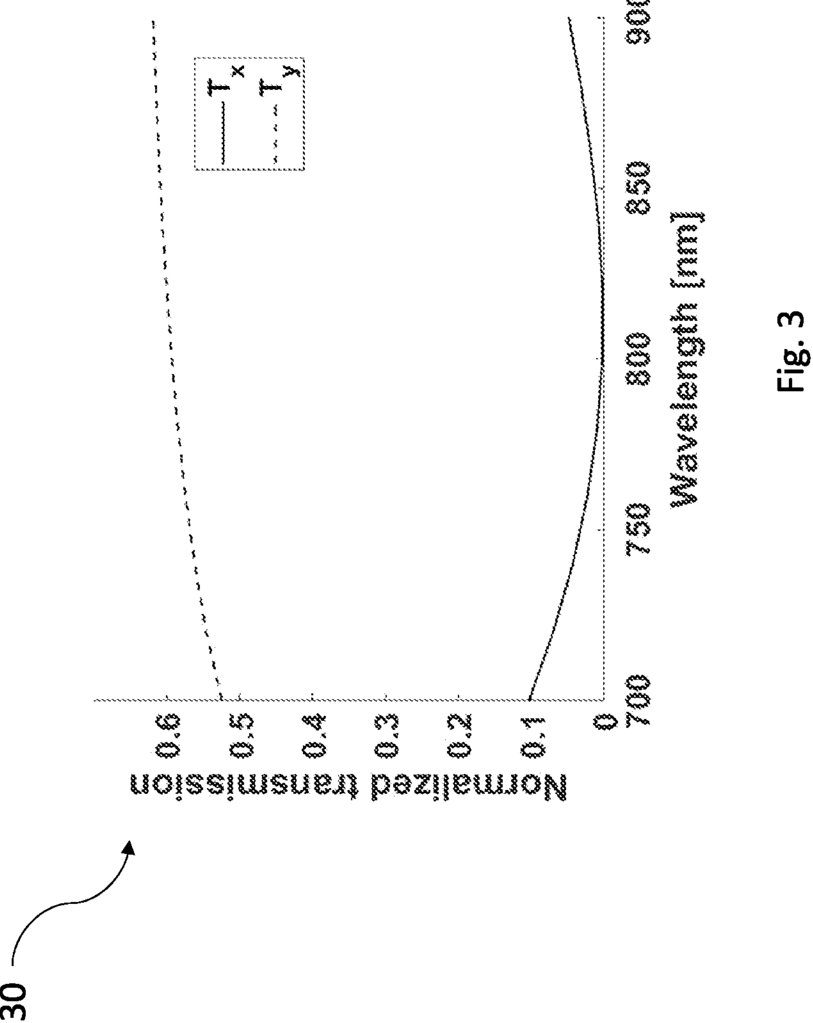
FIG. 3 is a graph showing the normalized transmission of two polarization states through the OMS of FIG. 2 plotted against the wavelength of the incident light.

FIG. 3 is a graph 30 showing the normalized transmission $T_y$, $T_x$, through the OMS 3 of the illustrated embodiment of the light polarized linearly along the Y axis 12, and the light linearly polarized along the X axis 14 respectively, plotted against the incident wavelength. It can be seen from the graph of FIG. 3 that at an incident wavelength of 800 nm, the normalized transmission $T_x \approx 0$. Whilst the light linearly polarized along the Y axis 12 is not fully transmitted, with the normalized transmission $T_y$ being between 0.5 and 0.6 across the wavelength range of 700 nm to 900 nm which is plotted, this transmission is significantly higher than any transmission of the light linearly polarized along the X axis 14, and so the OMS 3 is effective in providing the transmission characteristics outlined above.

Figure 4:
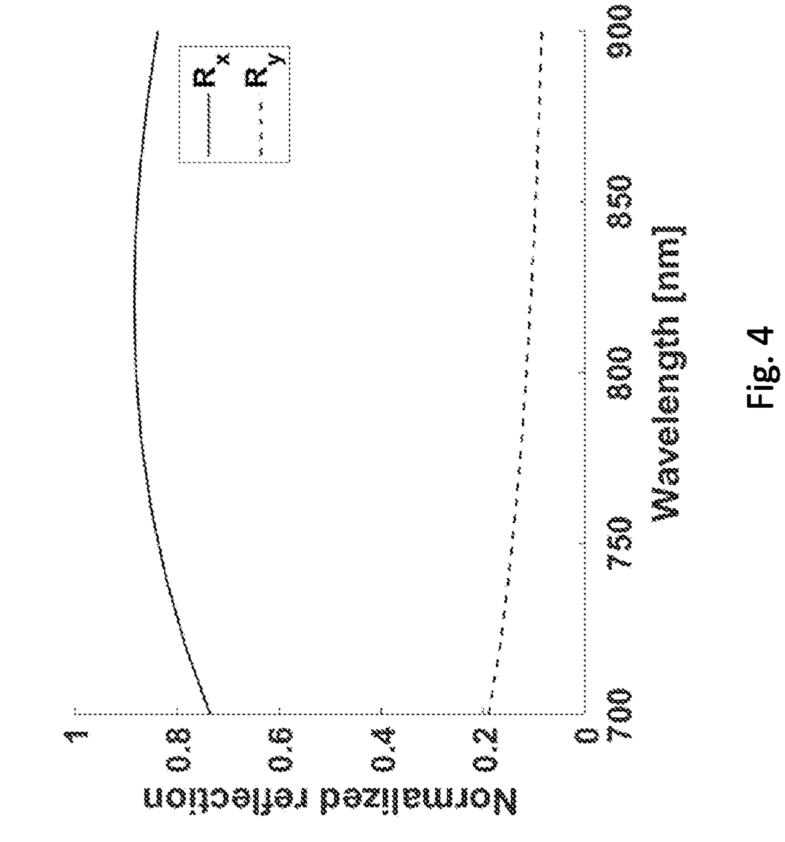
FIG. 4 is a graph showing the normalized reflection of two polarization states from the OMS of FIG. 2, plotted against the wavelength of the incident light.
Figure 4:
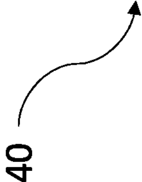

FIG. 4 is a graph 40 showing the normalized reflection $R_y$, $R_x$, from the OMS 3 of the illustrated embodiment of the light polarized linearly along the Y axis 12, and the light linearly polarized along the X axis 14 respectively, plotted against the incident wavelength. In the illustrated embodiment, the OMS 3 is configured to reflect light linearly polarized along the X axis 14, and to transmit light linearly polarized along the Y axis 12, and from the graph 40 of FIG. 4, it can be seen that the normalized reflection $R_x$ is much greater (>0.8 at 800 nm) than the normalized reflection $R_y$ (<0.2 at 800 nm), again illustrating that the OMS 3 is effective in providing the required characteristics.

Figure 5:
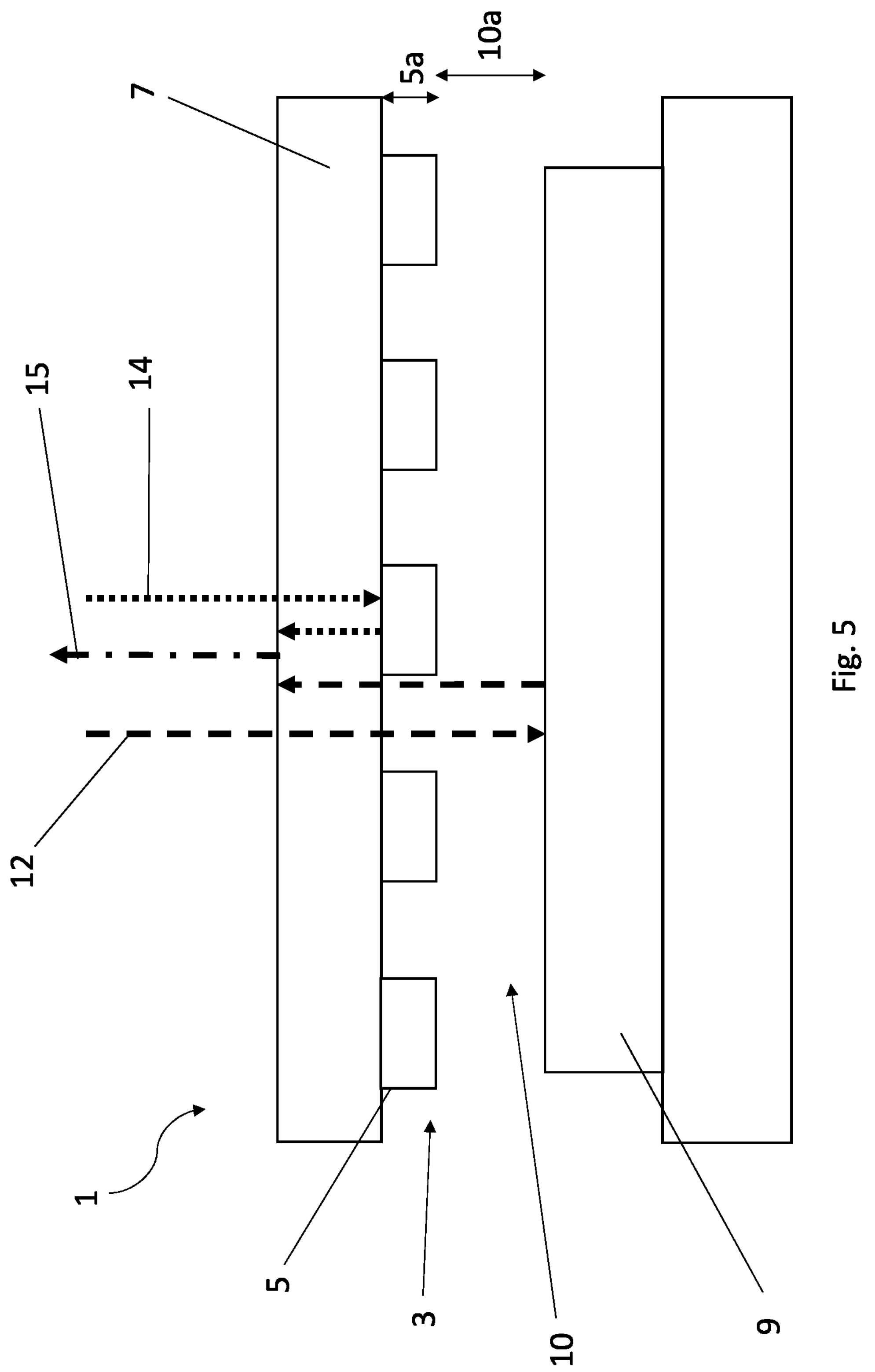
FIG. 5 shows the apparatus of FIG. 1 with the mirror in a raised position.

Operation of the device 1 will now be explained with reference to FIG. 1 and FIG. 5. FIG. 1 shows the waveplate apparatus 1 with the MEMS mirror 9 in a low position such that the gap 10 between the mirror 9 and the OMS 3 has a relatively large value 10*a*. FIG. 5 shows the waveplate apparatus 1 with the MEMS mirror 9 in a raised position such that the size 10*b* of the gap 10 between the mirror 9 and the OMS 3 is reduced. As has been discussed above, the OMS 3 substantially reflects the light linearly polarized along the X axis 14 and transmits the light linearly polarized along the Y axis 12 so that it is incident on the mirror 9. The light linearly polarized along the Y axis 12 is reflected by the mirror 9, and once again substantially transmitted by the OMS 3. In this way, after reflection from the waveplate apparatus 1, the light linearly polarized along the Y axis 12 (reflected by the mirror 9) combines with the light linearly polarized along the X axis 14 (reflected by the OMS 3) but with a phase difference associated with the additional optical path length to and from the mirror 9. The additional geometric path length is equal to twice the size 10*a* of the gap 10, plus twice the thickness 5*a* of the nanostructures 5, and it will be understood that the additional optical path length experienced by the light linearly polarized along the Y axis 12 is approximately equal to this additional physical path length. The optical path length is of course also dependent on the refractive index of the medium of the gap 10 (air in the illustrated embodiment), and the refractive index of the medium of the substrate 7.

Therefore, by adjusting the position of the mirror 9 relative to the OMS 3, as shown in FIG. 5, the additional path length and hence the phase difference between the reflected light linearly polarized along the X axis 14 and the reflected light linearly polarized along the Y axis 12 can be adjusted. The phase difference determines the polarization state of the resulting light 15 reflected from the waveplate apparatus and hence the polarization state of the reflected light 15 can be continuously adjusted by continuously adjusting the position of the mirror 9.

Figure 6:
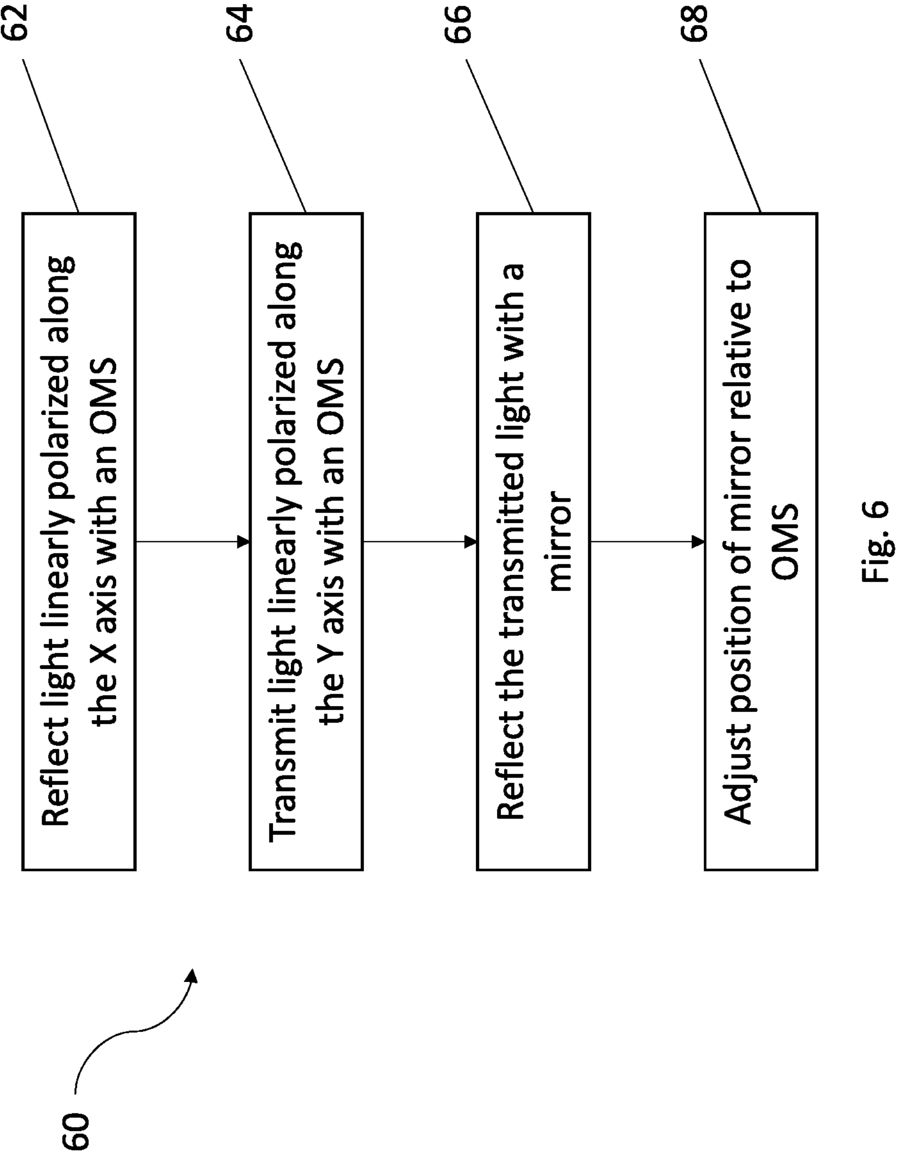
FIG. 6 is a flow diagram illustrating a method performed by the apparatus of FIG. 1.

The operation described above is summarized in the flowchart 60 of FIG. 6. At steps 62 and 64 the X and Y polarized light is respectively reflected and transmitted by the OMS 3. The transmitted Y polarized light is reflected by the mirror 9 at step 66 before being transmitted again by the OMS and combining interferometrically with the reflected X polarized light. At step 68 the position of the mirror 9 relative to the OMS 3 is adjusted to give an altered phase difference between X and Y polarizations and thus a different resultant polarization in the interferometric combination.

It will be understood that the explanation of the operation of the device 1 given above has been simplified for clarity, and that there will be reflections within the device in addition to those discussed above. The explanation only takes into account the first reflection from the mirror 9, but in reality, not all of the light reflected by the mirror 9 will be immediately transmitted back through the OMS 3. Rather, there is some reflection from both sides of the OMS 3 and so in theory there could be a large number of reflections back and forth between the mirror 9 and the OMS 3. For example, some light may be transmitted through the OMS 3, reflected from the mirror 9, and then re-transmitted through the OMS 3 immediately as discussed above. Also, some light may be transmitted through the OMS 3, reflected back and forth between the OMS 3 and the mirror 9 a plurality of times, and then transmitted back through the OMS 3. These reflections combine to form a total reflected signal according to the Fabry Perot equation (Equation 1). In the below equation, the medium of the substrate 7 has been designated '0', the medium of the gap 10 has been designated '1', and the medium of the mirror has been designated '2'. $r_{ab}$ is the reflection coefficient for light approaching the interface between media a and b from the side of medium a. $t_{ab}$ is the transmission coefficient for light approaching the interface between media a and b from the side of medium a. d is the thickness of medium 1 (the gap 10). λ is the wavelength of the light in medium 1. This equation is identical for both polarization states, however, the reflection and transmission coefficients themselves are dependent on the polarization. The coefficients are also dependent on the angle of the incident light, in this case the equation describes normal incidence.

$$r_{total} = r_{01} + \frac{t_{01}t_{10}r_{12}e^{i2\beta}}{1 - r_{10}r_{12}e^{i2\beta}} \quad (1)$$

$$\beta = \frac{2\pi}{\lambda}d$$

Figure 7:
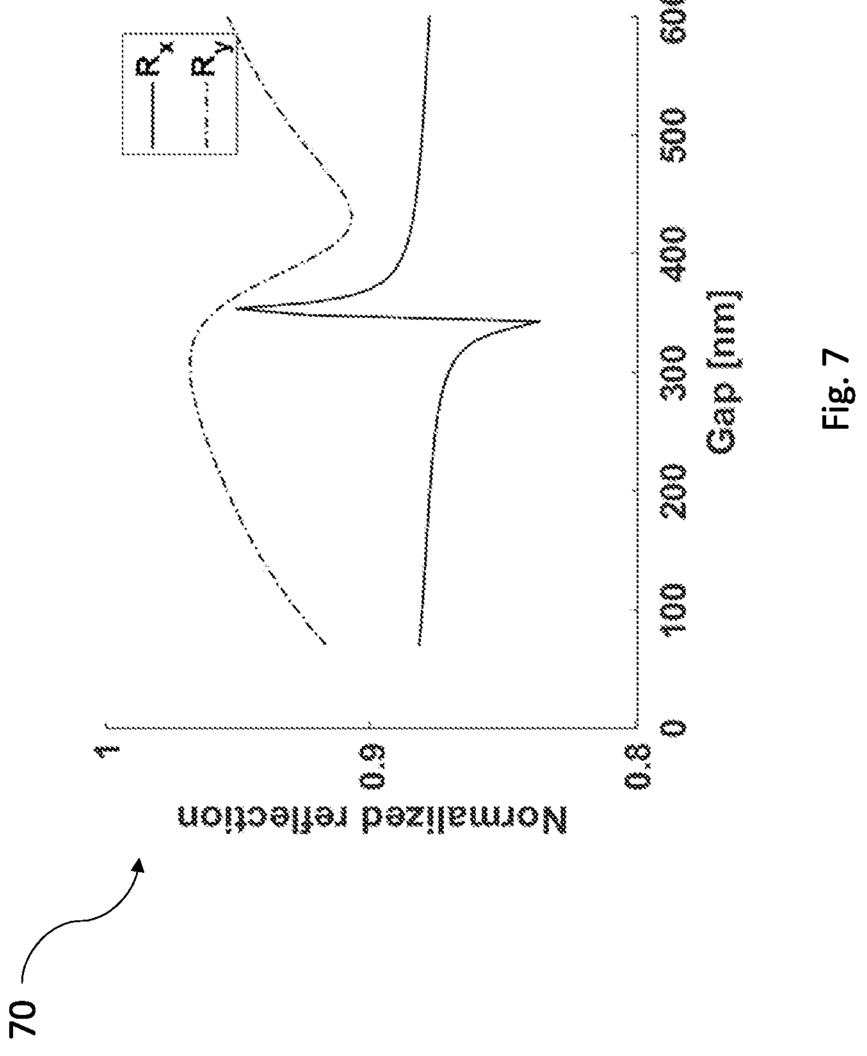
FIG. 7 is a graph showing the normalized reflection of two polarization states from the apparatus of FIG. 1, plotted against the size of the gap.

FIG. 7 shows the normalized reflection of both the light linearly polarized along the X axis $R_x$ and the light linearly polarized along the Y axis $R_y$, plotted against the gap size 10*a*.

The light linearly polarized along the X axis 14 is predominantly reflected by the OMS 3, and so it can be seen that for large portions of the graph, $R_x$ does not vary significantly with gap size 10*a*. There is however an anomalous trough and subsequent spike around a gap size of 350 nm. This is caused by the portion of the light linearly polarized along the X axis 14 which is transmitted by the OMS 3, reflected by the mirror 9, and then retransmitted by the OMS 3 interfering with the light linearly polarized along the X axis 14 initially reflected from the OMS when the path difference is equal to a whole wavelength (at a gap size 10*a* of 350 nm).

Similarly, although the light linearly polarized along the Y axis 12 is predominantly transmitted by the OMS 3, a portion of the light linearly polarized along the Y axis 12 is reflected by the OMS 3, and so the variation of $R_y$ with gap size 10*a* seen in FIG. 7 is associated with interference effects between the light linearly polarized along the Y axis 12 which is transmitted by the OMS 3, reflected by the mirror 9, and then retransmitted by the OMS 3, and the light linearly polarized along the Y axis 12 which is initially reflected from the OMS 3.

The OMS of the illustrated embodiment more effectively reflects the light linearly polarized along the X axis 14 than it transmits the light linearly polarized along the Y axis 12, and hence the interference effects shown in FIG. 7 are more pronounced for $R_y$ than for $R_x$.

Figure 8:
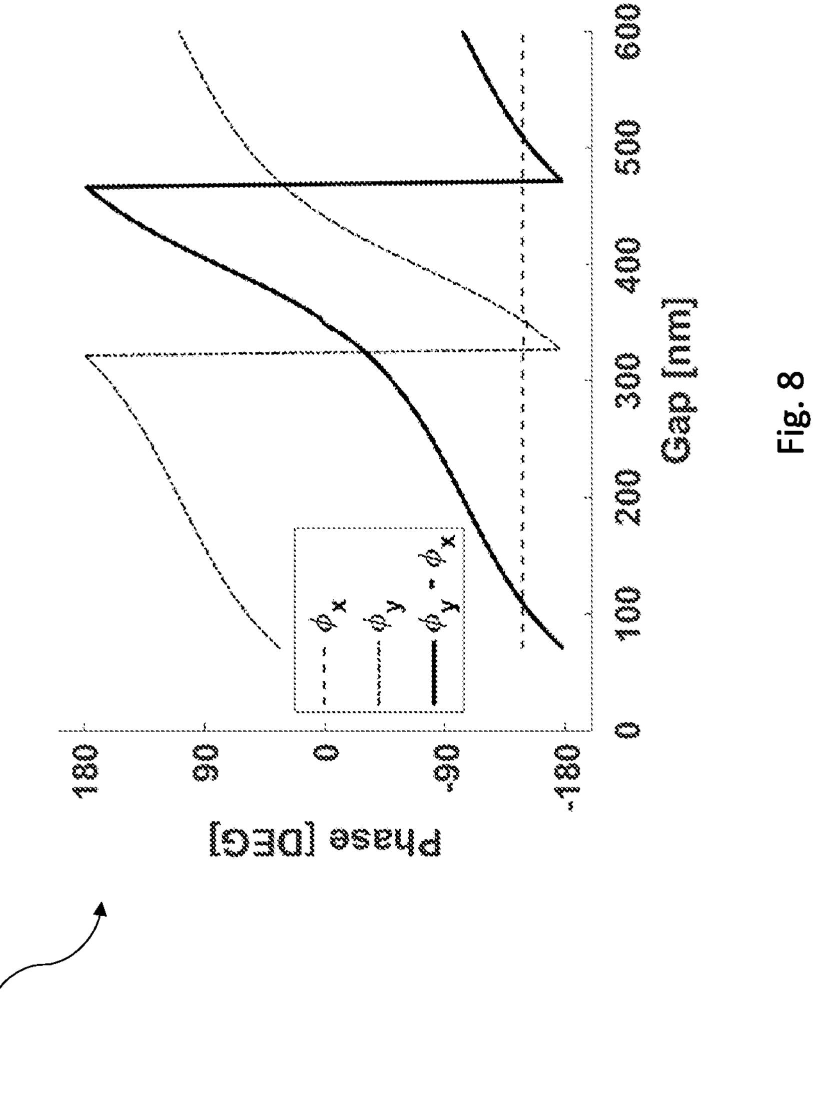
FIG. 8 is a graph showing the phase of two polarization states, and the phase difference between the two polarization states plotted against the size of the gap when using the apparatus of FIG. 1, incorporating the OMS of FIG. 9.

FIG. 8 is a graph 80 showing the phase of the light reflected by the waveplate apparatus 1, plotted against the size of the gap 10. It can be seen from the graph 80 that the phase $\phi_x$ of the light linearly polarized along the X axis 14 does not depend on the gap size. This is because, in the illustrated embodiment, the light linearly polarized along the X axis is mostly reflected by the OMS 3, not by the mirror 9. Meanwhile, the phase $\phi_y$ of the light linearly polarized along the Y axis 12 does change with the size of the gap 10. This is because, as explained above, the light linearly polarized along the Y axis 12 is mostly transmitted by the OMS and reflected by the mirror 9, and so has an additional path length which varies with the size of the gap 10. In the illustrated embodiment, the nanostructure thickness 5*a* is 50 nm. The graph 80 was created using a simulation of light with a wavelength of 800 nm.

The graph 80 also shows the phase difference, $\phi_y - \phi_x$, between the light linearly polarized along the Y axis 12, and the light linearly polarized along the X axis 14. The difference $\phi_y - \phi_x$ should be zero when the additional optical path length experienced by the light linearly polarized along the Y axis 12 is equal to the wavelength, which in the illustrated embodiment occurs for a gap size of approximately 350 nm. Such a result can be seen in graph 80.

Figure 9:
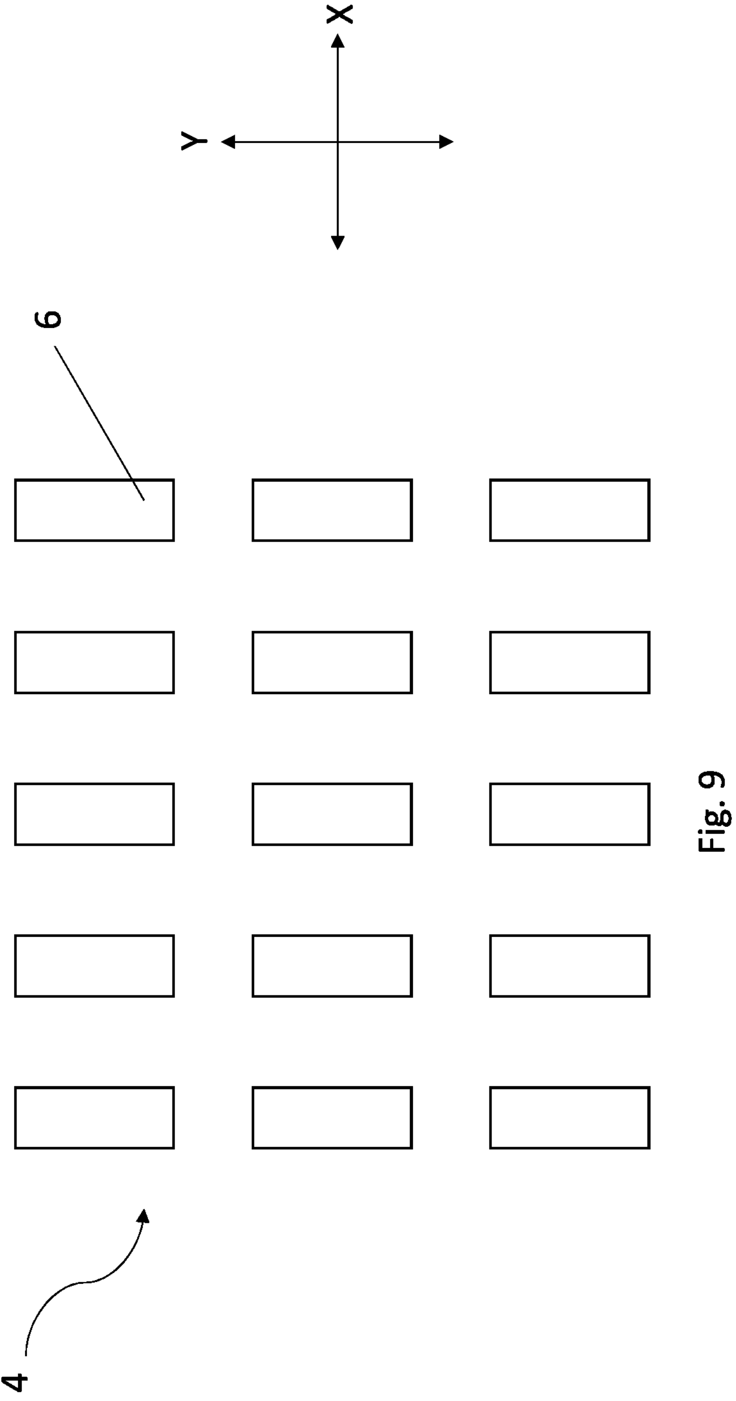
FIG. 9 shows an OMS with an alternative nanostructure geometry to that shown in FIG. 2.

The OMS 3 discussed above is simply an example of an OMS configuration that can be used in a waveplate apparatus 1 according to the invention. The OMS 3 is configured to predominantly reflect light of the first polarization, and transmit light of the second polarization. FIG. 9 illustrates an OMS 4 which is configured to reflect and transmit light of a first polarization state according to a first reflection/transmission factor, and to reflect and/or transmit light of a second polarization state according to a second reflection/transmission factor. The OMS 4 is formed of nanostructures 6.

In the illustrated embodiment each nanostructure 6 is made of gold, and has dimensions of 200 nm by 80 nm, with a thickness of 50 nm. The nanostructures 5 are arranged in a 2-dimensional array with a periodicity of 250 nm. The specific configuration in the illustrated embodiment is designed to perform best when the incident light is monochromatic and has a wavelength of 640 nm. It will be understood that although the specific embodiment being described is designed to perform best when the incident light has a wavelength of 640 nm, the invention is applicable using incident light of a wide range of wavelengths. In particular, the use of incident light having greater wavelengths may help to realize deeper tissue penetration.

Figure 10:
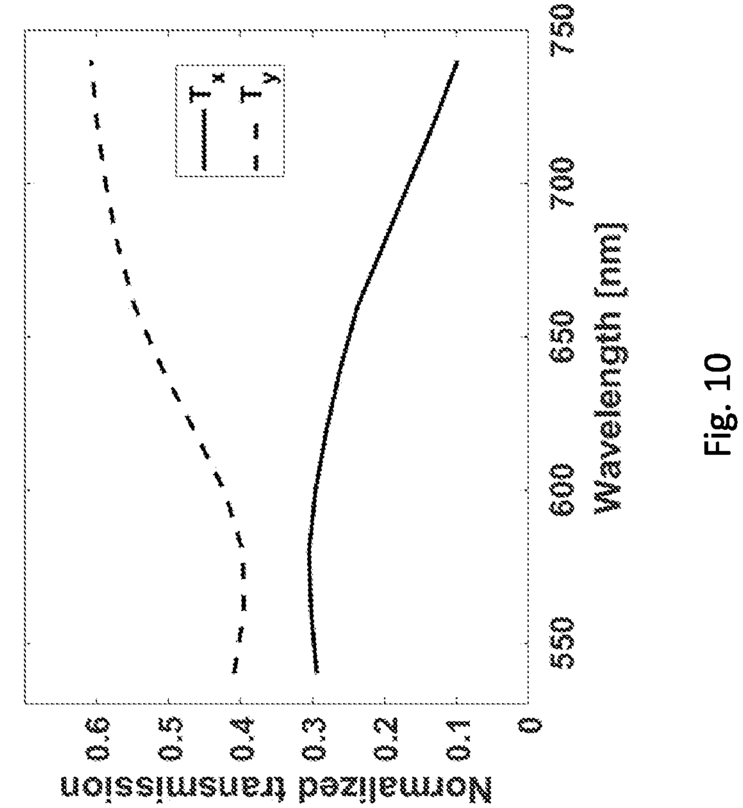
FIG. 10 is a graph showing the normalized transmission of two polarization states through the OMS of FIG. 9, plotted against the wavelength of the incident light.
Figure 10:
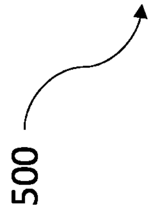

FIG. 10 is a graph 500 showing the normalized transmission $T_y$, $T_x$, through the OMS 4 of the illustrated embodiment of the light polarized linearly along the Y axis 12, and the light polarized linearly along the X axis 14 respectively, plotted against the incident wavelength. For this example, the embodiment has been optimized for light with wavelength 640 nm, and it can be seen from the graph of FIG. 10 that the behavior is different from the example in FIG. 3. In this case there is a significant but different transmission efficiency for both polarization states, and the difference of the transmission and reflection (seen in FIG. 11) amplitudes for the two polarization states has been optimized for switching between mirror and half-waveplate behavior.

Figure 11:
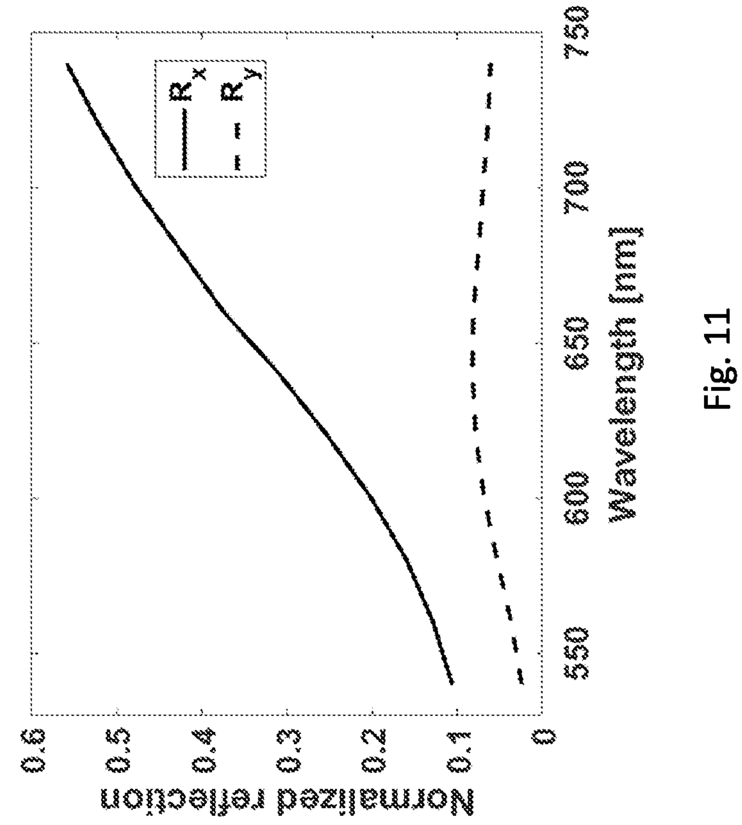
FIG. 11 is a graph showing the normalized reflection of two polarization states through the OMS of FIG. 9, plotted against the wavelength of the incident light.

FIG. 11 is a graph 600 showing the normalized reflection $R_y$, $R_x$, from the OMS 4 of the illustrated embodiment of the light polarized linearly along the Y axis 12, and the light linearly polarized along the X axis 14 respectively, plotted against the incident wavelength. For this example, the embodiment has been optimized for light with wavelength 640 nm, and it can be seen from the graph of FIG. 11 that the behavior is different from the example in FIG. 4. In this case there is a significant but different reflection efficiency for both polarization states (i.e., the OMS 4 has a first and second reflection/transmission factor which are different), and the difference of the transmission (seen in FIG. 10) and reflection amplitudes for the two polarization states has been optimized for switching between mirror and half-waveplate behavior of the embodiment which can be seen in FIG. 14.

Figure 12:
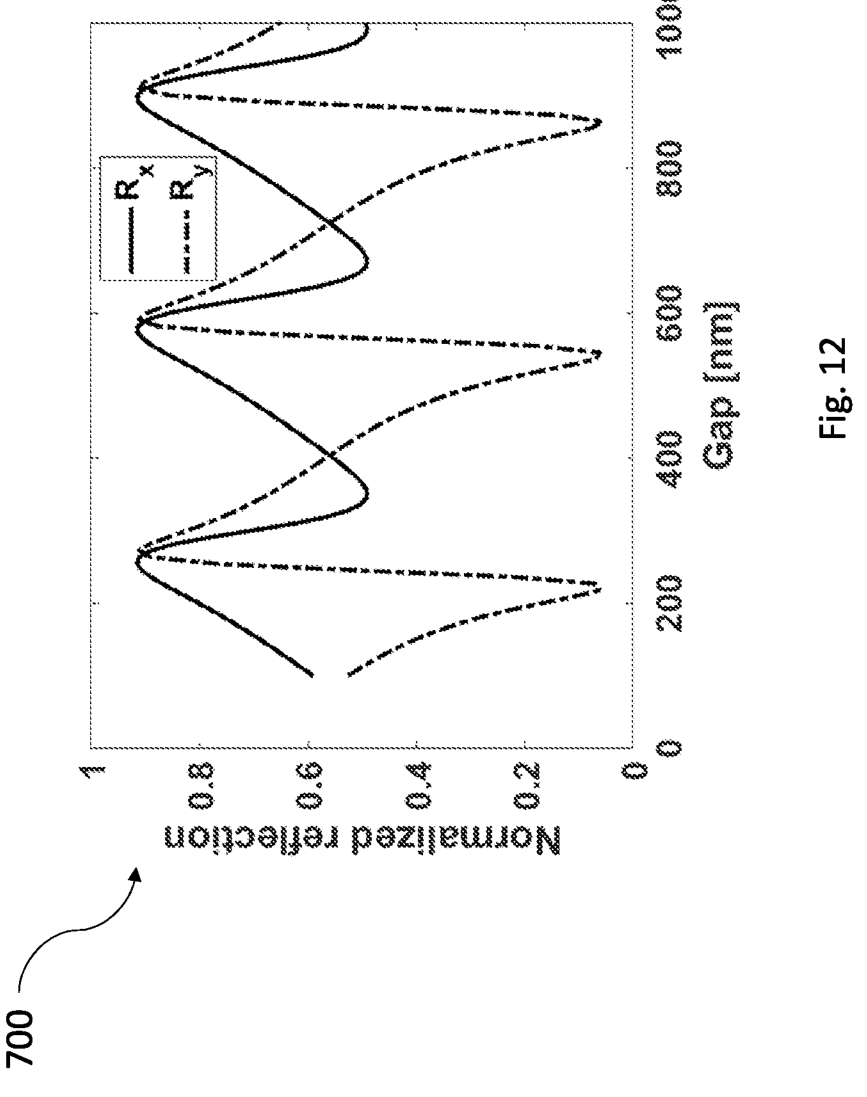
FIG. 12 is a graph showing the normalized reflection of two polarization states from the apparatus of FIG. 1, incorporating the OMS of FIG. 9, plotted against the size of the gap.

FIG. 12 is a graph 700 showing the normalized reflection of both the light linearly polarized along the X axis $R_x$ and the light linearly polarized along the Y axis $R_y$, plotted against the gap size 10*a*. This is for the example embodiment (using OMS 4) designed for switching between mirror and half-waveplate functionality for light with wavelength 640 nm.

Figure 13:
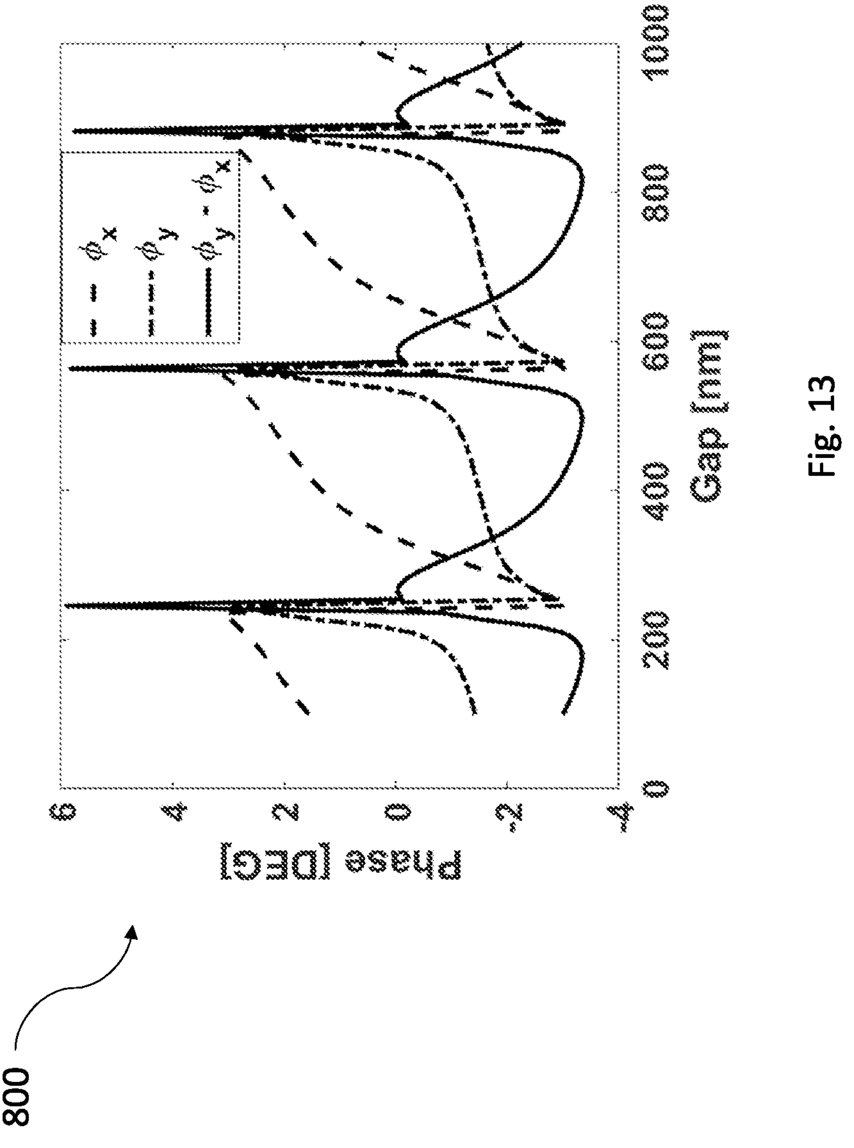
FIG. 13 is a graph showing the phase of two polarization states, and the phase difference between the two polarization states plotted against the size of the gap when using the apparatus of FIG. 1, incorporating the OMS of FIG. 9.

FIG. 13 is a graph 800 showing the phase of the light reflected by the waveplate apparatus 1, incorporating the OMS 4 of FIG. 9, plotted against the size of the gap 10*a*. This is for the example embodiment designed for switching between mirror and half-waveplate functionality for light with wavelength 640 nm. The functionality is not as obviously seen in graph 80 as in FIG. 8 for the example embodiment for light with wavelength 800 nm, but the functionality is more easily seen in FIG. 14.

Figure 14:
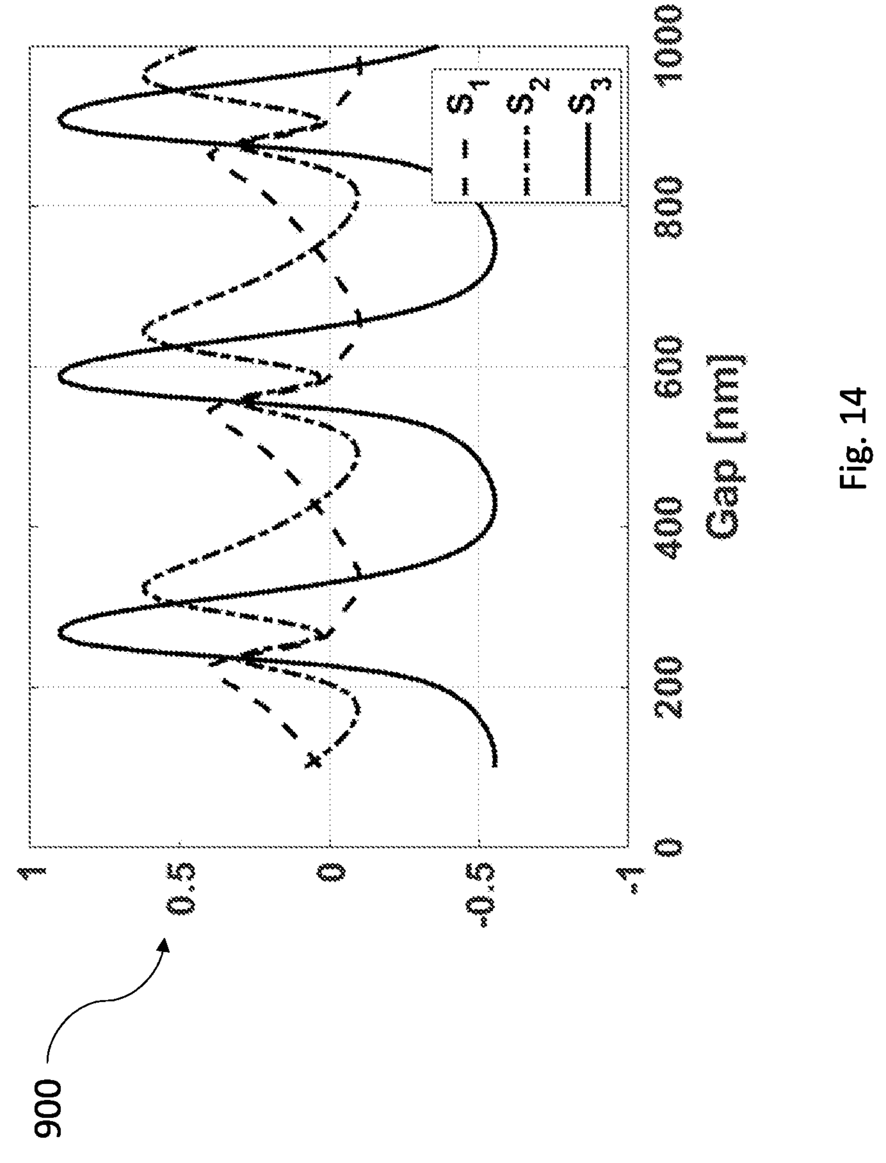
FIG. 14 is a graph showing the stokes parameters of the reflected light from the apparatus of FIG. 1, incorporating the OMS of FIG. 9, for a specific incoming polarization state, plotted against the size of the gap.

FIG. 14 is a graph 900 showing the Stokes parameters for light reflected from the apparatus 1, incorporating the OMS 4 of FIG. 9, designed for light with wavelength 640 nm, plotted against the gap size 10*a*. The incident light is circularly polarized with Stokes components S1=0, S2=0, S3=1. As can be seen from the graph 900, the function of the embodiment switches between that of a mirror and that of a half-waveplate where S1=0, S2=0 and S3 is either at a maximum or minimum.

Figure 15:
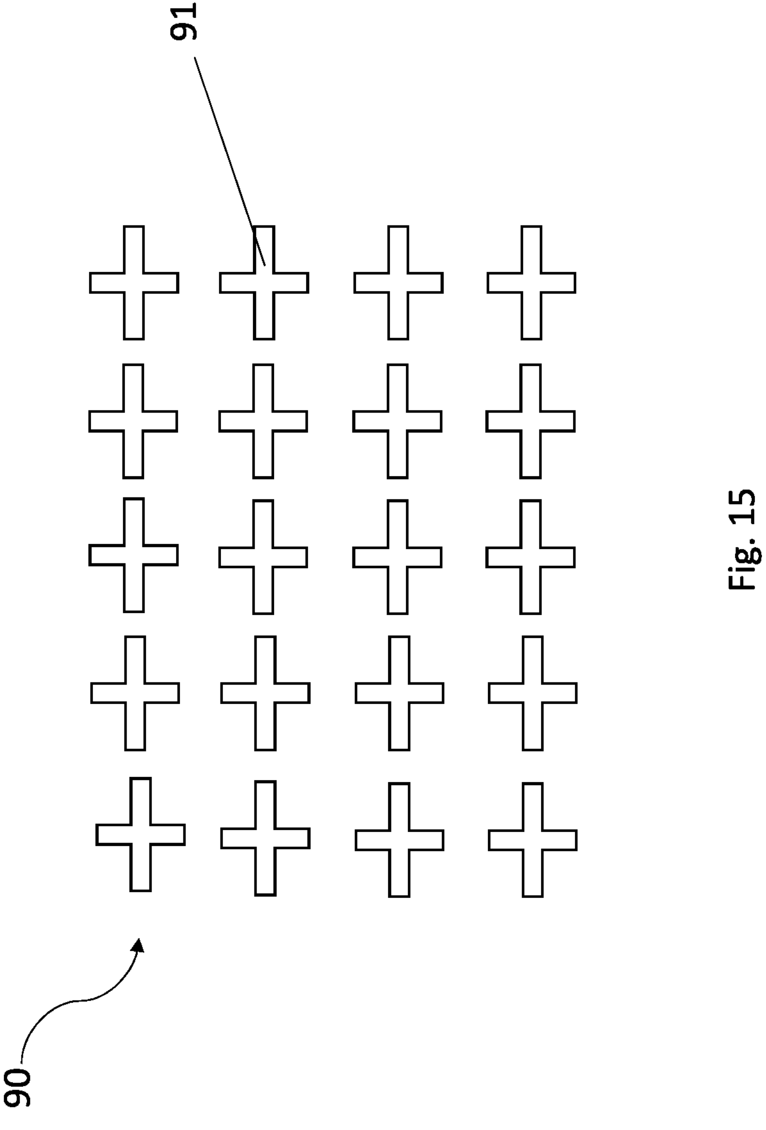
FIG. 15 shows a further OMS with an alternative nanostructure geometry to those shown in FIG. 2 and FIG. 9.

FIG. 15 is a schematic plan view diagram of an OMS 90 with an alternative structure to that of OMS 3 and OMS 4 shown in FIGS. 2 and 9. The OMS 90 comprises individual nanostructures 91 which have a cross-shaped footprint. In another possible variant the nanostructures could be L shaped.

Figure 16:
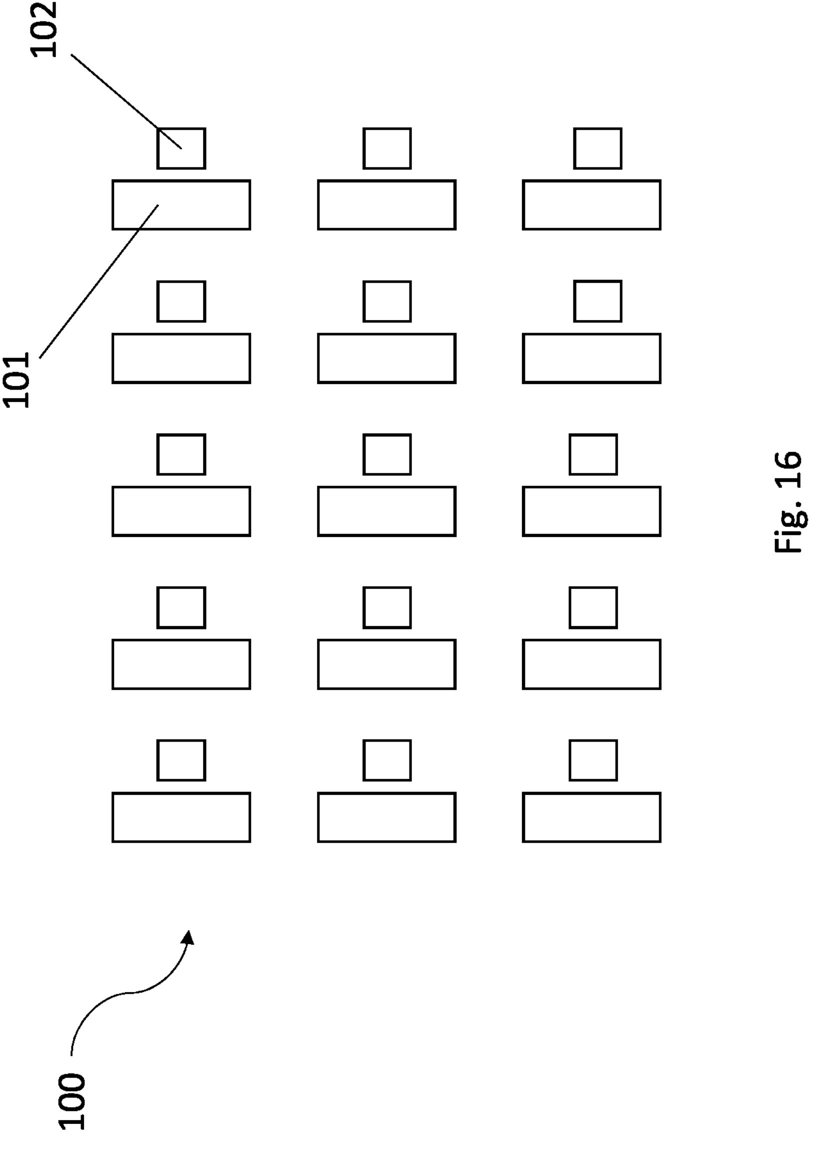
FIG. 16 shows another OMS with an alternative nanostructure geometry.

FIG. 16 is a schematic plan view diagram of a further OMS 100. The OMS 100 comprises individual first nanostructures 101 and second nanostructures 102. First nanostructures 101 have a rectangular footprint, and each first nanostructure 101 is accompanied by a second nanostructure 102 which is smaller than the first nanostructure 101, and has a square or rectangular footprint.

Figure 17:
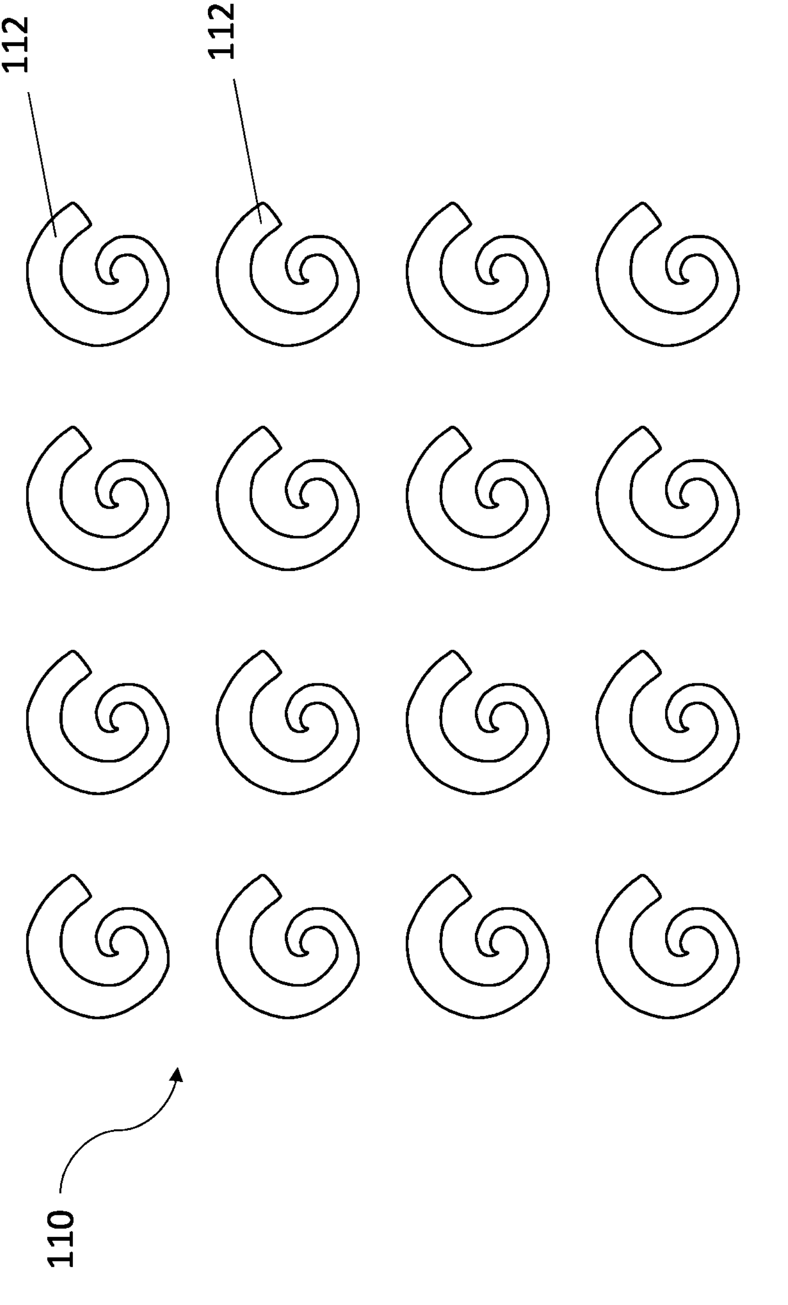
FIG. 17 shows another OMS with an alternative nanostructure geometry.

FIG. 17 is a schematic plan view diagram of a further OMS 110. The OMS 110 comprises individual nanostructures 112 which have a spiral-shaped footprint to interact with incident light that has left or right handed circular polarization. The transmitted circular polarization will change handedness when reflected by the mirror 9, but when approaching the spirals 112 from the other side the spirals 112 will also change handedness, thereby allowing the polarization to be transmitted back through the OMS 110.

As with the embodiments of FIG. 2 and FIG. 9, the nanostructures 91, 101, 102, 112 of FIGS. 15, 16 and 17 have maximum dimensions less than the wavelength of the incident light and are arranged in vertical and horizontal periodically repeating patterns with spatial periods less than the wavelength of the incident light.

The OMS geometries shown in FIGS. 15, 16, and 17 are presented as examples, and it will be understood that OMS's with different geometries may be used in place of the OMS 3 of the illustrated embodiment. More complex geometries such as those shown in FIGS. 15, 16, and 17, give more degrees of freedom when designing the OMS which for example, can allow the functionality of the OMS to be made more broadband.

Further, in the illustrated embodiment, the OMS is constructed from gold, but the skilled person will understand that other metals may be used provided that the nanostructures can be fabricated using the metal. For example, aluminum may be used.

Figure 18:
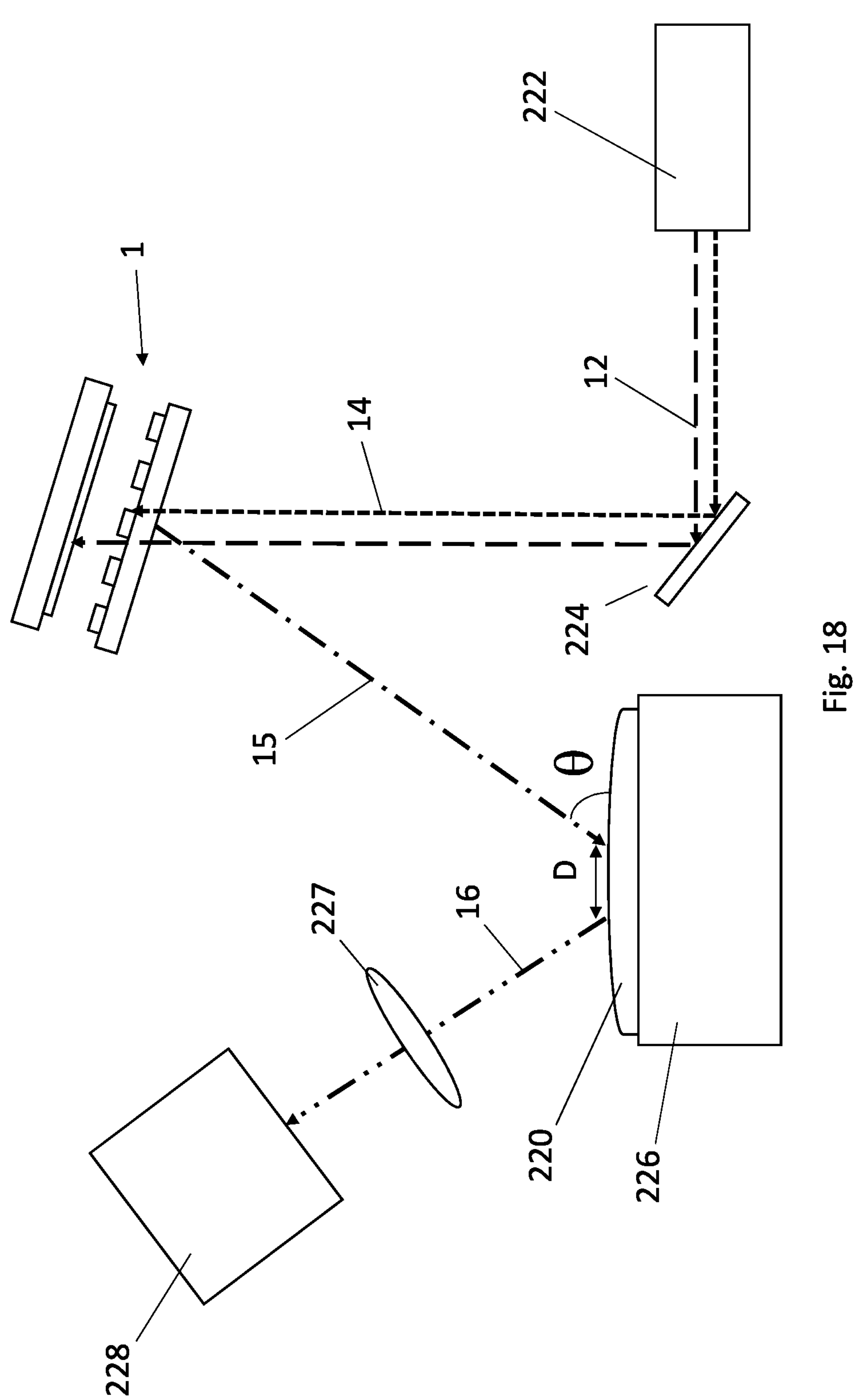
FIG. 18 shows a system in accordance with the present invention.

FIG. 18 is a schematic diagram of a system 200 for analyzing a cell or tissue sample 220. The system comprises a monochromatic light source 222, a redirecting mirror 224, the waveplate apparatus 1 of FIG. 1, a sample translation stage 226 on which the sample is placed, collection optics, which in the illustrated embodiment comprises a lens 227, and a polarimeter 228. Although any suitable polarimeter may be used, in the illustrated embodiment, the polarimeter 228 is a metasurface based polarimeter, as explained further below.

In the illustrated embodiment, the light source 222 emits linearly polarized light monochromatic light which contains both light, which is linearly polarized along the Y axis 12, and light which is linearly polarized along the X axis 14. The light is initially incident on the redirecting mirror 224 which is angled to direct the light towards the waveplate apparatus 1.

The waveplate apparatus 1 then modifies the polarization state of the light as discussed above, and directs the light onto the cell or tissue sample 220 which is supported on the sample translation stage 226.

For tissue imaging, circularly polarized light may be preferable. As such, the waveplate apparatus 1 may be configured to manipulate the light incident on the waveplate apparatus 1 by making the light linearly polarized in the X axis 14 and light linearly polarized along the Y axis 12 $\pi/2$ out of phase with each other.

The light 15 enters the sample 220 and interacts with the cellular or extracellular structures therein, for example, with the cell nucleus which is typically enlarged in cancerous cells. The optical properties of these structures (e.g., the scattering and the absorption coefficients $\mu_s$ and $\mu_a$, the anisotropy factor g and the refractive index n) will vary depending on the disease state of the sample.

As such, the light 16 which is reflected from the sample has a polarization state which is determined by the structures within the sample 220 and thus is indicative of the disease state of the sample.

As can be seen in FIG. 18, the point at which the light 15 is incident on the sample (the illumination point) and the point from which the reflected light 16 is collected (the collection point) are separated by a distance D at the surface of the sample. By providing this distance D, the light 16 being collected has penetrated the sample 220 and undergone diffusive scattering. Thus, the light 16 has interacted with the sample sufficiently to result in the polarization altering effects upon which the invention relies. The distance D may range from 0 to some quantity that provides better visualization and tissue differentiation capability. The extent of difference D may depend on a sample's optical properties and thickness.

The distance D may depend on the penetration depth (i.e., the depth which the light 15 reaches within the sample 220). The penetration depth can be controlled by controlling the angle of incidence θ. A larger value of θ will result in a greater penetration depth. The angle of incidence can be controlled by mounting the apparatus 1 on a holder (not shown) which is able to tilt the apparatus 1 relative to the sample 220. Alternatively, or additionally, the angle of incidence may be controlled by altering the angle of the mirror 9. Larger wavelengths allow for greater penetration depths.

The sample translation stage 226 is configured to translate (i.e., move) the sample 220 such that the light 15 can be made incident on different points on the sample 220. This allows the build-up of a polarimetric image map, by point-by-point polarimetric measurement. In other embodiments, the sample translation state 226 may be replaced with a simple stationary plinth, and the system may be arranged to scan the light 15 across the sample 220, avoiding the need for a translation stage.

Figure 19:
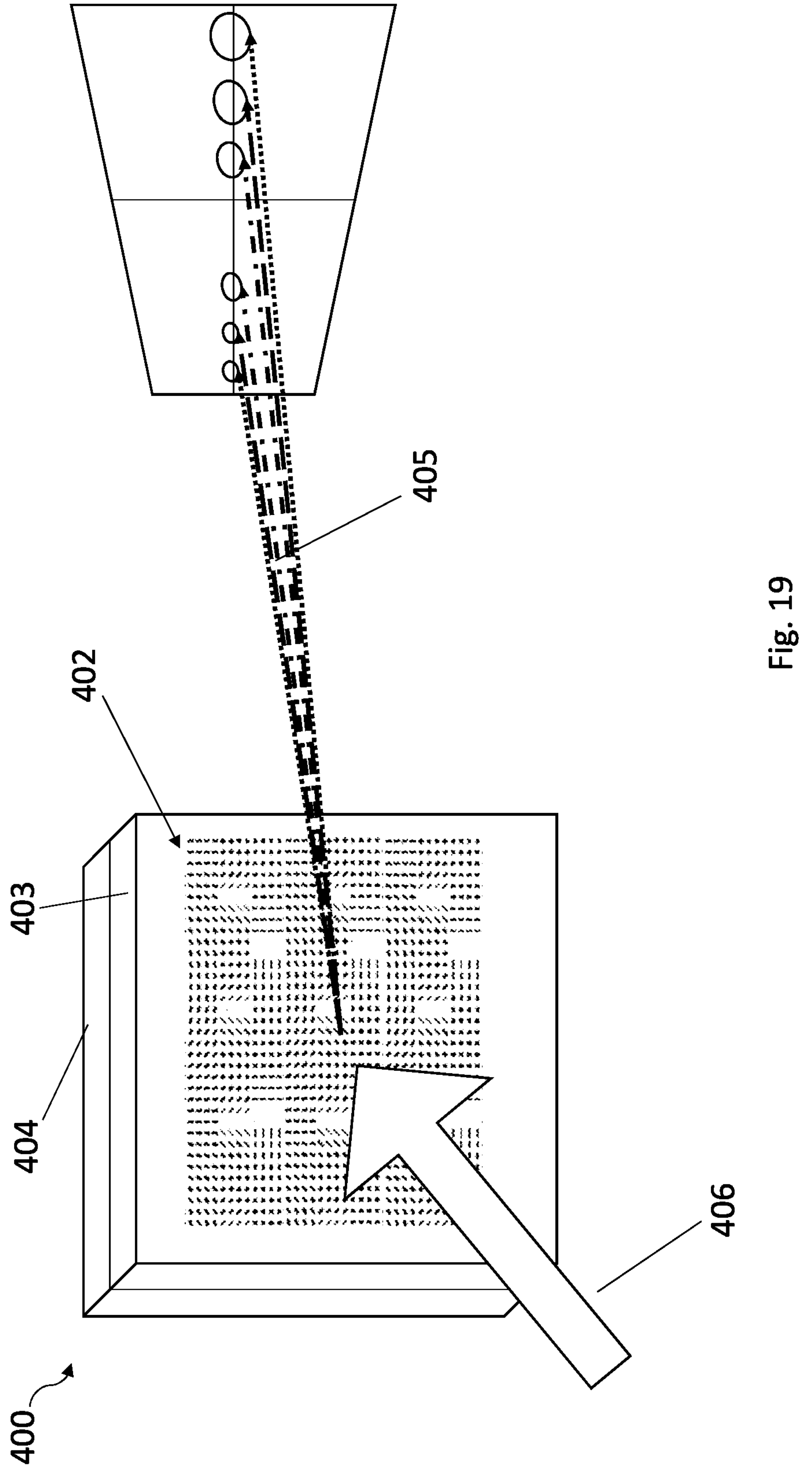
FIG. 19 shows a metasurface based polarimeter for use in the system of FIG. 18.

The polarimeter 228 is arranged to receive the light 16 which is reflected from the sample and analyze the polarization state of said light. In the illustrated embodiment, the light 16 is focused onto the polarimeter 228 by lens 227. Any suitable polarimeter may be used for this purpose, but in particularly advantageous embodiments, the polarimeter 228 may be a metasurface based polarimeter. By using a metasurface based polarimeter, the miniaturization advantages which are associated with the use of the waveplate apparatus 1 can be further extended to the polarimeter 228. An exemplary metasurface based polarimeter 400 is described below with reference to FIG. 19.

The polarimeter 400 comprises a nanostructure 402 which is placed on a thin dielectric layer 403 and substrate 404. In the illustrated embodiment, both the nanostructure 402, and the substrate 404 are formed of gold, although other suitable materials are envisaged. The nanostructure 402 forms an optical metasurface which is configured to split incoming light 16 into component polarization states 405, according to orthogonal polarization bases (e.g., linearly polarized along the Y axis, linearly polarized along the X axis; linearly polarized along the two diagonal axes 45 degrees rotated compared to the X and Y axes; left and right handed circular polarized). This splitting is done by selectively diffracting different polarization components into spatial domains with distinct spot contrasts. By measuring the intensities of these spatially separated component beams it is possible to calculate the overall polarization state of the incoming light 16. The illustrated embodiment 400 interleaves grating patterns that reflect three sets of orthogonal polarization states to six different positions along a line. This polarimeter is therefore not suited for measuring spectral information, but the incoming polarization state can be determined by measuring the relative intensities of the six spots on the detector, which may for example, be a 1D or a 2D array of light sensitive pixels. If the gratings are not perfectly efficient, there will be another reflected beam corresponding to secularly reflected light, this spot may be ignored or used for calibration, and has not been drawn in FIG. 19.

The invention claimed is:

1. A system for analyzing a cell or tissue sample using polarized light, the system comprising:

an apparatus for adjustably changing the polarization state of incident light having at least a first wavelength containing a first polarization state and a second polarization state;

a light source arranged to provide the incident light to the apparatus; and a polarimeter, wherein the apparatus is arranged to direct polarized light onto a cell or tissue sample, and the polarimeter is arranged to receive light reflected from the cell or tissue sample, and measure the polarization state of said light, wherein the apparatus comprises:

a polarization changing optical metasurface (OMS) arranged to reflect and/or transmit light of a first polarization state according to a first reflection/transmission factor, and to reflect and/or transmit light of a second polarization state according to a second reflection/transmission factor, said second polarization state being different from said first polarization state, and said second reflection/transmission factor being different from said first reflection/transmission factor; and a mirror arranged to reflect the transmitted light of the first and/or second polarization states, wherein the apparatus is arranged to move the mirror and/or the polarization changing OMS relative to one another to alter a separation between the polarization changing OMS and the mirror, thereby altering a phase difference between the light reflected by the polarization changing OMS and the light reflected by the mirror such that a combined polarization state of light reflected by the apparatus is adjustable.

2. The system of claim 1, wherein the polarization changing OMS is configured to predominantly reflect light of the first polarization, and transmit light of the second polarization.

3. The system of claim 1, wherein the first and second reflection/transmission factors are independent of the separation between the polarization changing OMS and the mirror.

4. The system of claim 1, wherein the apparatus is arranged such that said separation between the polarization changing OMS and the mirror has a minimum value of at least 10% of the first wavelength.

5. The system of claim 1, wherein the apparatus is arranged such that the separation between the polarization changing OMS and the mirror has a maximum value of at most 10 times the first wavelength.

6. The system of claim 1, wherein the apparatus is arranged to alter the separation between the polarization changing OMS and the mirror between respective minimum and maximum values which differ by at least 9/10 of the first wavelength.

7. The system of claim 1, wherein the polarization changing OMS is arranged to transmit less than 10% of the light of the first polarization state, and to transmit more than 40% of the light of the second polarization state.

8. The system of claim 1, wherein the polarization changing OMS is arranged such that the first polarization is orthogonal to the second polarization.

9. The system of claim 1, arranged to move the mirror relative to the polarization changing OMS.

10. The system of claim 9, wherein the mirror is a micro-electromechanical systems mirror.

11. The system of claim 1 wherein the apparatus is a waveplate apparatus.

12. The system of claim 1, wherein the polarimeter is a metasurface-based polarimeter.

13. The system of claim 1, wherein the system is arranged to alter an angle of incidence of the polarized light onto the cell or tissue sample.

14. The system of claim 1, further comprising collection optics configured to direct light reflected from the cell or tissue sample onto the polarimeter.

15. A method of analyzing a cell or tissue sample using polarized light, the method comprising:

providing incident light from a light source having at least a first wavelength containing a first polarization state and a second polarization state;

reflecting and/or transmitting light from said incident light having a first polarization state, according to a first reflection/transmission factor, with a polarization changing optical metasurface (OMS);

reflecting and/or transmitting light from said incident light having a second polarization state, according to a second reflection/transmission factor, with said polarization changing OMS, said second polarization state being different from said first polarization state and said second reflection/transmission factor being different from said first reflection/transmission factor;

reflecting the transmitted light of the first and/or second polarization states with a mirror;

moving the mirror and/or the polarization changing OMS in order to alter a separation between the polarization changing OMS and the mirror thereby altering a phase difference between the light reflected by the polarization changing OMS and the light reflected by the mirror such that a combined polarization state of light reflected by both the polarization changing OMS and the mirror is adjusted;

directing the light reflected by the OMS and the mirror, which has a combined polarization state, onto said cell or tissue sample;

reflecting light from the cell or tissue sample onto a polarimeter; and measuring the polarization state of said reflected light to analyze the cell or tissue sample.

16. A system for analyzing a body area using polarized light, the system comprising:

an apparatus for adjustably changing the polarization state of incident light having at least a first wavelength containing a first polarization state and a second polarization state;

a light source arranged to provide the incident light to the apparatus; and a polarimeter, wherein the apparatus is arranged to direct polarized light onto a body area, and the polarimeter is arranged to receive light reflected from the body area, and measure the polarization state of said light, wherein the apparatus comprises:

a polarization changing optical metasurface (OMS) arranged to reflect and/or transmit light of a first polarization state according to a first reflection/transmission factor, and to reflect and/or transmit light of a second polarization state according to a second reflection/transmission factor, said second polarization state being different from said first polarization state, and said second reflection/transmission factor being different from said first reflection/transmission factor; and a mirror arranged to reflect the transmitted light of the second polarization state, wherein the apparatus is arranged to move the mirror and/or the polarization changing OMS relative to one another to alter a separation between the polarization changing OMS and the mirror, thereby altering a phase difference between the light reflected by the polarization changing OMS and the light reflected by the mirror such that a combined polarization state of light reflected by the apparatus is adjustable.

17. A method of analyzing a body area using polarized light, the method comprising: providing incident light from a light source having at least a first wavelength containing a first polarization state and a second polarization state;

reflecting and/or transmitting light from said incident light having a first polarization state, according to a first reflection/transmission factor, with a polarization changing optical metasurface (OMS);

reflecting and/or transmitting light from said incident light having a second polarization state, according to a second reflection/transmission factor, with said polarization changing OMS, said second polarization state being different from said first polarization state and said second reflection/transmission factor being different from said first reflection/transmission factor;

reflecting the transmitted light of the first and/or second polarization states with a mirror;

moving the mirror and/or the polarization changing OMS in order to alter a separation between the polarization changing OMS and the mirror thereby altering a phase difference between the light reflected by the polarization changing OMS and the light reflected by the mirror such that a combined polarization state of light reflected by both the polarization changing OMS and the mirror is adjusted;

directing the light reflected by the OMS and the mirror which has a combined polarization state onto said body area;

reflecting light from the body area onto a polarimeter; and measuring the polarization state of said reflected light to analyze the body area.

* * * * *